US009988746B2

(12) United States Patent
Dong et al.

(10) Patent No.: US 9,988,746 B2
(45) Date of Patent: Jun. 5, 2018

(54) PARTIALLY DEGRADABLE FIBERS AND MICROVASCULAR MATERIALS FORMED FROM THE FIBERS

(71) Applicant: The Board of Trustees of the University of Illinois, Urbana, IL (US)

(72) Inventors: Hefei Dong, Urbana, IL (US); Stephen J. Pety, Urbana, IL (US); Nancy R. Sottos, Champaign, IL (US); Jeffrey S. Moore, Savoy, IL (US); Scott R. White, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 575 days.

(21) Appl. No.: 14/040,287

(22) Filed: Sep. 27, 2013

(65) Prior Publication Data

US 2014/0162519 A1    Jun. 12, 2014

Related U.S. Application Data

(60) Provisional application No. 61/708,149, filed on Oct. 1, 2012.

(51) Int. Cl.
*D03D 25/00* (2006.01)
*A61F 2/02* (2006.01)
(Continued)

(52) U.S. Cl.
CPC .............. *D03D 25/005* (2013.01); *A61F 2/02* (2013.01); *D03D 15/00* (2013.01); *H01M 2/145* (2013.01);
(Continued)

(58) Field of Classification Search
CPC ...... B29C 70/10; D03D 15/00; D03D 25/005; Y10T 442/3195; Y10T 442/3106;
(Continued)

(56) References Cited

U.S. PATENT DOCUMENTS 6,766,817 B2    7/2004 da Silva
7,569,625 B2    8/2009 Keller et al.
(Continued)

FOREIGN PATENT DOCUMENTS

WO    2007005657    1/2007

OTHER PUBLICATIONS

Esser-Kahn, A. P., Thakre, P. R., Dong, H., Patrick, J. F., Vlasko-Vlasov, V. K., Sottos, N. R., Moore, J. S. and White, S. R. (2011), Three-Dimensional Microvascular Fiber-Reinforced Composites. Adv. Mater., 23: 3654-3658. doi:10.1002/adma.201100933, Published Jul. 15, 2011.*
(Continued)

*Primary Examiner* — Jennifer A Steele
(74) *Attorney, Agent, or Firm* — Haukaas Fortius PLLC; Michael H. Haukaas

(57) ABSTRACT

A partially degradable polymeric fiber includes a thermally degradable polymeric core and a coating surrounding at least a portion of the core. The thermally degradable polymeric core includes a polymeric matrix including a poly(hydroxyalkanoate), and a metal selected from the group consisting of an alkali earth metal and a transition metal, in the core polymeric matrix. The concentration of the metal in the polymeric matrix is at least 0.1 wt %. The partially degradable polymeric fiber may be used to form a microvascular system containing one or more microfluidic channels.

20 Claims, 16 Drawing Sheets

(51) Int. Cl.
  *H01M 2/16* (2006.01)
  *H01M 2/14* (2006.01)
  *H01M 10/052* (2010.01)
  *D03D 15/00* (2006.01)
  *B01J 3/00* (2006.01)
  *B01L 3/00* (2006.01)

(52) U.S. Cl.
  CPC ......... *H01M 2/162* (2013.01); *H01M 2/1653* (2013.01); *B01L 3/502707* (2013.01); *D10B 2509/00* (2013.01); *H01M 10/052* (2013.01); *Y10T 428/294* (2015.01); *Y10T 428/2933* (2015.01); *Y10T 442/30* (2015.04)

(58) Field of Classification Search
  CPC ......... Y10T 442/3154; Y10T 442/3163; Y10T 442/3146; Y10T 442/64; Y10T 442/641; Y10T 442/637; Y10T 442/654; Y10T 442/612; Y10T 428/2929
  See application file for complete search history.

(56) References Cited

U.S. PATENT DOCUMENTS

| | | | |
|---|---|---|---|
| 2003/0119398 A1* | 6/2003 | Bogdanovich | B29C 70/24 442/204 |
| 2007/0087198 A1* | 4/2007 | Dry | B29C 73/22 428/408 |
| 2008/0003433 A1 | 1/2008 | Mikami | |
| 2008/0305343 A1* | 12/2008 | Toohey | B29C 73/22 428/447 |
| 2009/0191402 A1 | 7/2009 | Beiermann et al. | |
| 2013/0065042 A1 | 3/2013 | Esser-Kahn et al. | |

OTHER PUBLICATIONS

Celgard, LLC; Polypore Company, "Celgard 2325—Product Information", 2012, Publisher: Celgard, LLC.; A Polypore Company.
E.I. Du Pont De Nemours and Company, "DuPont Kapton: Polyimide Film", 2012, Publisher: E.I. du Pont de Nemours and Company.
E.I. Du Pont De Nemours and Company, "DuPOnt Fuel Cells: DuPont Nafion PFSA Membranes", 2009, Publisher: E.I. du Pont de Nemours and Company.
Momentive Specialiaty Chemicals Inc., "EPON Resin 828", 2005, Publisher: Momentive Specialiaty Chemicals Inc.
De Espinosa, Lucan Montero et al., "Plant oils: The perfect renewable resource for polymer science?!", 2011, pp. 837-852, vol. 47, Publisher: European Polymer Journal.
OSHA and ANSI, "Material Safety Data Sheet—According to OSHA and ANSI", May 28, 2011, Publisher: OSHA and ANSI.
Momentive Technical Data Sheet, "Epikure Curing Agent 3300", Aug. 2007, Publisher: Momentive Specialiaty Chemicals Inc.
Momentive Specialiaty Chemicals Inc., "Epikure Epoxy Curing Agents", 2013, Publisher: Momentive Specialty Chemicals Inc.
Bin Zhao et al., "Control and Applications of Immiscible Liquids in Microchannels", 2002.
Toohey, Kathleen S. et al., "Delivery of Two-Part Self-Healing Chemistry via Microvascular Networks," Advanced Functional Materials, vol. 19, 2009, pp. 1399-1405.
Toohey, Kathleen S. et al., "Self-Healing Materials With Microvascular Networks," Nature Materials, vol. 6, Aug. 2007, pp. 581-585.

* cited by examiner

PARTIALLY DEGRADABLE FIBERS AND MICROVASCULAR MATERIALS FORMED FROM THE FIBERS

REFERENCE TO RELATED APPLICATIONS

This application claims the benefit of U.S. Provisional Application No. 61/708,149 entitled "Partially Degraded Fibers And Microvascular Materials Formed From The Fibers" filed Oct. 1, 2012, which is incorporated by reference in its entirety.

FEDERALLY SPONSORED RESEARCH OR DEVELOPMENT

This invention was made with government support under contract numbers FA9550-10-1-0255, awarded by the Air Force Office of Scientific Research, and DOE ANL 9F-31921, awarded by the Energy Frontier Research Centers (EFRC). The government has certain rights in the invention.

BACKGROUND

Synthetic composite materials possess desirably high strength-to-weight ratios; however, synthetic composites typically have lacked dynamic functionality that occurs in natural composite materials. Natural composite materials can utilize vascular networks to accomplish a variety of biological functions, in both soft and hard tissue. For example, composite structures such as bone tissue or wood are lightweight and have high strength, yet contain extensive vasculature capable of transporting mass and energy.

Another feature of natural composite materials is their ability to have different levels of communication between distinct vascular networks, depending on the specific role of the material within an organism. In one example, the phloem and xylem channels of plant vascular bundles may be independent and separated by lignin layers, such that the contents of the channels do not interact. In another example, physical contact between the artery and vein channels of a human or animal circulatory system may provide for heat transfer between the channels; however, the chemical compositions of the fluids in these channels remain separate. In yet another example, gas exchange of oxygen and carbon dioxide occurs between the blood vessel channels and the alveoli channels within the lungs.

An ongoing challenge in materials science is the development of microvascular networks in synthetic materials using conventional manufacturing processes. Specialized fabrication methods such as laser-micromachining, soft lithography, templating with degradable sugar fibers, and incorporating hollow glass or polymeric fibers can produce some microvascular structures in synthetic materials. These specialized methods, however, are not currently suitable for rapid, large-scale production of materials having complex vasculatures.

In one approach to microfluidic materials, relatively short microfluidic channels are provided in a matrix in the form of hollow glass fibers (WO 2007/005657 to Dry). The glass fibers are present as repair conduits containing a fluid that can heal a crack in the composite matrix. A significant limitation of this approach is the brittle nature of the hollow glass fibers, which limits the shapes and lengths of microfluidic channels that can be present in the material. In addition, the glass fibers cannot readily be used to form a microfluidic network.

In another approach to microfluidic materials, microfluidic channels are formed in a polymeric matrix by arranging hollow polymeric fibers and then forming the matrix around the hollow polymeric fibers (U.S. Publication No. 2008/0003433 to Mikami). Hollow polymeric fibers may offer a wider variety of microfluidic channel shapes than those available from hollow glass fibers. This approach, however, also has a number of limitations, including an inability to form a network from the individual hollow fibers, the relatively small number of materials available as hollow fibers, and the possibility of incompatibility between the hollow fiber and the matrix.

Microfluidic networks can be formed in a polymeric matrix using a three-dimensional (3-D) direct-write assembly technique (U.S. Publication No. 2008/0305343 to Toohey et al.). While this fabrication method provides excellent spatial control, the resulting networks typically will not survive the mechanical and/or thermal stresses encountered in the conventional processes of forming reinforced composites.

It is desirable to provide multiple microvascular networks in synthetic materials, where the type and level of communication between the distinct microvascular networks can be varied between different materials. It is desirable for such complex microvascular networks to be formed using conventional manufacturing processes. It also is desirable for the microfluidic channels of the different networks within a material to be available in a variety of shapes and dimensions, and for a variety of polymers to be available as the polymeric matrix of such composites.

SUMMARY

In one aspect, there is provided a partially degradable polymeric fiber that includes a thermally degradable polymeric core and a coating surrounding at least a portion of the core. The thermally degradable polymeric core includes a polymeric matrix including a poly(hydroxyalkanoate), and a metal selected from the group consisting of an alkali earth metal and a transition metal, in the core polymeric matrix. The concentration of the metal in the polymeric matrix is at least 0.1 wt %.

In another aspect, there is provided a method of making a partially degradable polymeric fiber that includes combining a fiber containing a poly(hydroxyalkanoate) and having an exterior surface, and a composition containing a fluorinated fluid and a metal selected from the group consisting of an alkali earth metal and a transition metal. The method further includes maintaining the fiber and the composition together at a temperature and for a time sufficient to provide a concentration of the metal in the fiber of at least 0.1 wt %, separating the fiber and the fluorinated fluid, and depositing a layer of a material on at least a portion of the exterior surface of the fiber.

In another aspect, there is provided a partially degradable fiber system that includes a thermally degradable polymeric core and a coating surrounding at least a portion of the core. The thermally degradable polymeric core has a degradation temperature of at most 250° C. At least a portion of the coating does not thermally degrade at temperatures below 275° C.

In another aspect, there is provided a microvascular system that includes a solid polymeric matrix including a first material, and a woven structure in the matrix. The woven structure includes a plurality of microfluidic channels having a channel wall including a second material, where the second material is different from the first material.

In another aspect, there is provided a method of making a microvascular system that includes forming a composite including a solid polymeric matrix, and a plurality of partially degradable polymeric fibers in the matrix. The partially degradable polymeric fibers include a thermally degradable polymeric core having a degradation temperature of at most 250° C., and a coating surrounding at least a portion of the thermally degradable polymeric core, where at least a portion of the coating does not thermally degrade at temperatures below 275° C. The method further includes heating the composite to a temperature of from 100 to 250° C., maintaining the composite at a temperature of from 100 to 250° C. for a time sufficient to form degradants from the polymeric core, and removing the degradants from the composite to provide a network of microfluidic channels. The degradants have an average molecular weight less than 500 Daltons.

In a further aspect, there is provided a method of making a microporous film that includes providing a coating precursor including a thermally degradable polyhydroxyalkanoate having a degradation temperature of at most 250° C., and a thermally stable material that does not thermally degrade at temperatures below 275° C. The method further includes casting a film of the coating precursor, solidifying the coating precursor, and heating the film to a temperature of from 100° C. to 250° C. for a time sufficient to form degradants from the thermally degradable polyhydroxyalkanoate. The method also includes removing the degradants from the film to provide a microporous film. The microporous film may serve as separator in energy storage devices such as lithium-ion batteries.

BRIEF DESCRIPTION OF THE DRAWINGS

The subject matter of the present application can be better understood with reference to the following drawings and description. The components in the figures are not necessarily to scale and are not intended to accurately represent molecules or their interactions, emphasis instead being placed upon illustrating the principles of the subject matter of the present application. Moreover, in the figures, like referenced numerals designate corresponding parts throughout the different views.

DETAILED DESCRIPTION

In one aspect, a partially degradable polymeric fiber includes a thermally degradable polymeric core and a coating surrounding at least a portion of the core. The partially degradable polymeric fiber may be used to form a microvascular system having a solid polymeric matrix and a woven structure in the matrix, where the woven structure includes a plurality of microfluidic channels having a channel wall, which may have any of a variety of permeability properties.

Such microvascular systems can provide unprecedented applications, and can be designed to contain a variety of microvascular network types and sizes—from simple, straight conduits to complex, computer-controlled 3D woven architectures. The microvascular systems may be formed from commercially available materials, and may be integrated seamlessly with conventional fiber-reinforced composite manufacturing methods.

A microvascular system may be formed from composite materials containing partially degradable polymeric fibers and optionally containing reinforcing fibers. Partially degradable polymeric fibers may be used to form biomimetic material systems in a reliable manner, and may be used to model, reproduce and/or extend transport functions performed by microvascular systems in nature. Composite materials containing both partially degradable polymeric fibers and reinforcing fibers can be used to provide microvascular systems, such as those described above.

A partially degradable polymeric fiber may include a thermally degradable polymeric core that degrades at temperatures above those typically used for forming composite materials, but below the typical degradation temperatures of composite materials. The thermally degradable polymeric core may be at least partially surrounded by a coating, where at least a portion of the coating does not thermally degrade at the same temperatures as the core. The thermally degradable polymeric core may include a polymeric fiber matrix and a catalyst in the fiber matrix that lowers the degradation temperature of the matrix polymer to within an appropriate temperature window.

Partially Degradable Polymeric Fibers

Figure 1:
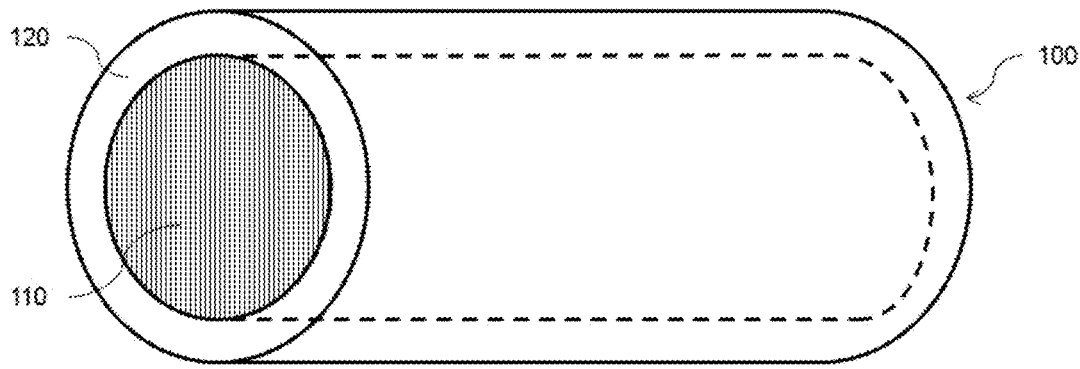
FIG. 1 depicts a partially degradable polymeric fiber.

FIG. 1 depicts a schematic representation of a partially degradable polymeric fiber 100, which includes a thermally degradable polymeric core 110 and a coating 120 surrounding at least a portion of the thermally degradable polymeric core. The thermally degradable polymeric core 110 includes a polymeric matrix. Preferably the polymeric matrix of the core 110 has a degradation temperature of at most 250° C., whereas at least a portion of the coating 120 preferably does not thermally degrade at temperatures below 275° C.

Partially degradable polymeric fibers, such as fiber 100, preferably have a combination of desirable properties. These desirable properties include sufficient strength for configuration as a preform and/or for combination with a composite matrix precursor using standard composite formation methods, and mechanical integrity at temperatures typically used to form composites. The desirable properties also include degradation and volatilization temperatures within a range between the highest composite matrix solidification temperatures and the lowest thermal degradation temperatures of the composite matrix. Preferably the partially degradable polymeric fiber has all of these desirable properties.

The thermally degradable polymeric core 110 preferably has a degradation temperature below 280° C., and preferably has a degradation temperature of at most 250° C. Preferably the thermally degradable polymeric core 110 has a degradation temperature between 100 and 250° C. Preferably the thermally degradable polymeric core 110 has a degradation temperature of at most 220° C., of at most 180° C., of at most 150° C., or of at most 100° C.

The thermally degradable polymeric core 110 may include a poly(hydroxyalkanoate). A poly(hydroxyalkanoate) is an aliphatic polyester having the general structure:

where n is an integer of at least 10, x is an integer from 0 to 4, and $R^1$-$R^4$ independently are —H or an alkyl group. Examples of poly(hydroxyalkanoate)s include poly(3-hydroxybutyrate) (P3HB), poly(4-hydroxybutyrate) (P4HB), poly(3-hydroxy-valerate) (PHV), polycaprolactone, poly(lactic acid) (PLA), poly(glycolic acid) (PGA), and copolymers of the monomeric units of these polymers.

It has now been discovered that thermally degradable poly(hydroxyalkanoate) fibers can be at least partially surrounded with a coating to produce partially degradable fibers, which can be used successfully as coated sacrificial fibers in polymeric matrices such as epoxies. These coated sacrificial fibers preferably include a thermally degradable fiber core having a polymeric fiber matrix including a poly(hydroxyalkanoate) and including a metal in the fiber matrix, where the metal includes an alkali earth metal and/or a transition metal. Preferably the concentration of the metal in the fiber matrix is at least 0.1 percent by weight (wt %).

Poly(hydroxyalkanoate)s may degrade at elevated temperatures through a depolymerization process, forming small molecule degradants that may be gases. For example, poly(lactic acid) (PLA) is a thermoplastic poly(hydroxyalkanoate) that depolymerizes at temperatures above 280° C., forming lactide as a gaseous degradant. The depolymerization temperature of poly(hydroxyalkanoate)s such as PLA may be reduced by blending the poly(hydroxyalkanoate) with an alkaline earth metal and/or a transition metal. A reduced depolymerization temperature may help prevent damage to materials in contact with the thermally degradable polymeric core 110, such as the coating 120 or a polymeric matrix in which the partially degradable polymeric fiber 100 is contained. Preferably the thermally degradable polymeric core 110 depolymerizes within an appropriate temperature range, but without deterioration of the desirable mechanical properties of the fiber 100 below the degradation temperature. Preferably the poly(hydroxyalkanoate) has a degradation temperature below 280° C., and preferably has a degradation temperature of at most 250° C.

Preferably the concentration of the metal in the poly(hydroxyalkanoate) fiber matrix is at least 0.2 wt %, at least 0.5 wt %, at least 1 wt %, at least 2 wt %, at least 2.5 wt %, at least 3 wt %, at least 5 wt %, at least 7 wt %, or at least 10 wt %. The concentration of the metal in the poly(hydroxyalkanoate) fiber matrix may be from 0.1 to 10 wt %, from 0.2 to 7 wt %, from 0.5 to 5 wt %, or from 1 to 3 wt %. Preferably the metal is present in the fiber as MgO, CaO, BaO, SrO, tin(II) acetate, tin(II) oxalate, tin(II) octoate, or scandium triflate (Sc(OTf)$_3$). More preferably the metal is present in the fiber as strontium oxide, tin(II) oxalate or tin(II) octoate.

The coating 120 that surrounds at least a portion of the core includes a polymeric material having a degradation temperature higher than the degradation temperature of the thermally degradable polymeric core 110. When the fiber 100 is heated to the degradation temperature of the thermally degradable polymeric core 110, the core will degrade and can be removed, providing a hollow fiber having a wall containing the polymeric material of the coating 120. Preferably, the coating 120 does not thermally degrade at temperatures below 250° C. Preferably, the coating 120 does not thermally degrade at temperatures below 275° C., at temperatures below 280° C., at temperatures below 300° C., at temperatures below 325° C., or at temperatures below 350° C.

The coating 120 may include a polyamide such as nylon; a polyester such as poly(ethylene terephthalate) and polycaprolactone; a polycarbonate; a polyether; an epoxy polymer; an epoxy vinyl ester polymer; a polyimide such as polypyromellitimide (for example KAPTON® (DuPont, Wilmington, Del.); a phenol-formaldehyde polymer such as bakelite (polyoxybenzylmethylenglycolanhydride; an amine-formaldehyde polymer such as a melamine polymer; a polysulfone; a polyacrylonitrile-butadiene-styrene) (ABS); a polyurethane; a polyolefin such as polyethylene, polystyrene, polyacrylonitrile, a polyvinyl, polyvinyl chloride and poly(DCPD); a polyacrylate such as poly(ethyl acrylate); a poly(alkylacrylate) such as poly(methyl methacrylate); a polysilane such as poly(carborane-silane); and/or a polyphosphazene.

The coating 120 may include an elastomer, such as an elastomeric polymer, an elastomeric copolymer, an elastomeric block copolymer, and/or an elastomeric polymer blend. Examples of elastomer polymers include polyolefins, polysiloxanes such as poly(dimethylsiloxane) (PDMS), polychloroprene, and polysulfides; examples of copolymer elastomers may include polyolefin copolymers and fluorocarbon elastomers; examples of block copolymer elastomers may include acrylonitrile block copolymers, polystyrene block copolymers, polyolefin block copolymers, polyester block copolymers, polyamide block copolymers, and polyurethane block copolymers; and examples of polymer blend elastomers include mixtures of an elastomer with another polymer.

The coating 120 may include a mixture of these polymers, including copolymers that include repeating units of two or more of the polymers, and/or including blends of two or more of the polymers. In one example, the coating 120 includes a blend of at least a first polymer and a second polymer, where the first polymer has a degradation temperature below 280° C., and the second polymer does not thermally degrade at temperatures below 280° C. In this example, one portion of the coating 120 may degrade at a temperature similar to the temperature at which the thermally degradable polymeric core 110 degrades, while another portion of the coating 120 may not degrade at this temperature. When such a coated fiber is heated to the degradation temperature of the first polymer of the coating, the thermally degradable polymeric core 110 and the portion of the coating containing the first polymer can degrade and can be removed, providing a hollow fiber having a wall containing the second polymer of the coating 120.

The coating 120 may include other ingredients in addition to the polymeric material. For example, the coating may contain one or more particulate fillers, stabilizers, antioxidants, flame retardants, plasticizers, colorants and dyes, fragrances, or adhesion promoters. An adhesion promoter is a substance that increases the adhesion between two substances, such as the adhesion between two polymers. One type of adhesion promoter that may be present includes substances that promote adhesion between the coating 120 and the thermally degradable polymeric core 110, and substances that promote adhesion between the coating 120 and a polymeric matrix in which the partially degradable polymeric fiber 100 is contained.

Methods of Making Partially Degradable Polymeric Fibers

Figure 2:
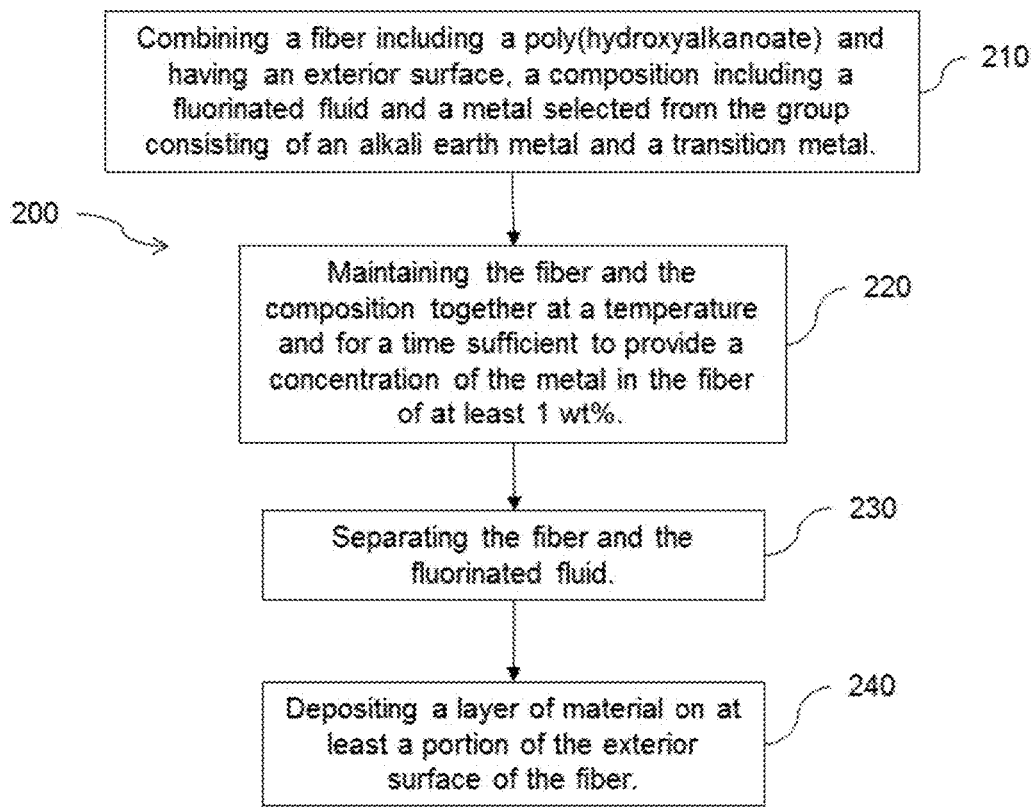
FIG. 2 is a schematic representation of a method of making a partially degradable fiber.

FIG. 2 illustrates a schematic representation of an example of a method of making a partially degradable fiber, such as the partially degradable fiber 100 of FIG. 1. Method 200 includes combining 210 a fiber including a poly(hydroxyalkanoate) and having an exterior surface, and a composition including a fluorinated fluid and a metal selected from the group consisting of an alkali earth metal and a transition metal. Method 200 further includes maintaining 220 the fiber and the composition together at a temperature and for a time sufficient to provide a concentration of the metal in the fiber of at least 0.1 wt %, separating 230 the fiber and the fluorinated fluid, and depositing 240 a layer of a material on at least a portion of the exterior surface of the fiber.

An alkali earth metal or a transition metal may be incorporated into a poly(hydroxyalkanoate) fiber through an infusion process, as outlined by the combining 210, maintaining 220 and separating 230 of method 200. In one example, PLA fibers may be infused with a tin(II) oxalate (SnOx) catalyst present in an aqueous trifluoroethanol (TFE) mixture. Exposing the PLA fibers to a solution of TFE:$H_2O$ using a ratio of 60:40 parts by volume (pbv) with 2% SnOx parts by weight (pbw), for a minimum of 24 h yielded partially degradable polymeric fibers suitable for use in the composite formation method of Vaporization of Sacrificial Components (VaSC). The catalyst-containing fibers converted to gas at a lower temperature and in less time than did pure PLA fibers, as measured by isothermal gravimetric analysis (iTGA), indicating a lower depolymerization onset temperature.

Figure 3:
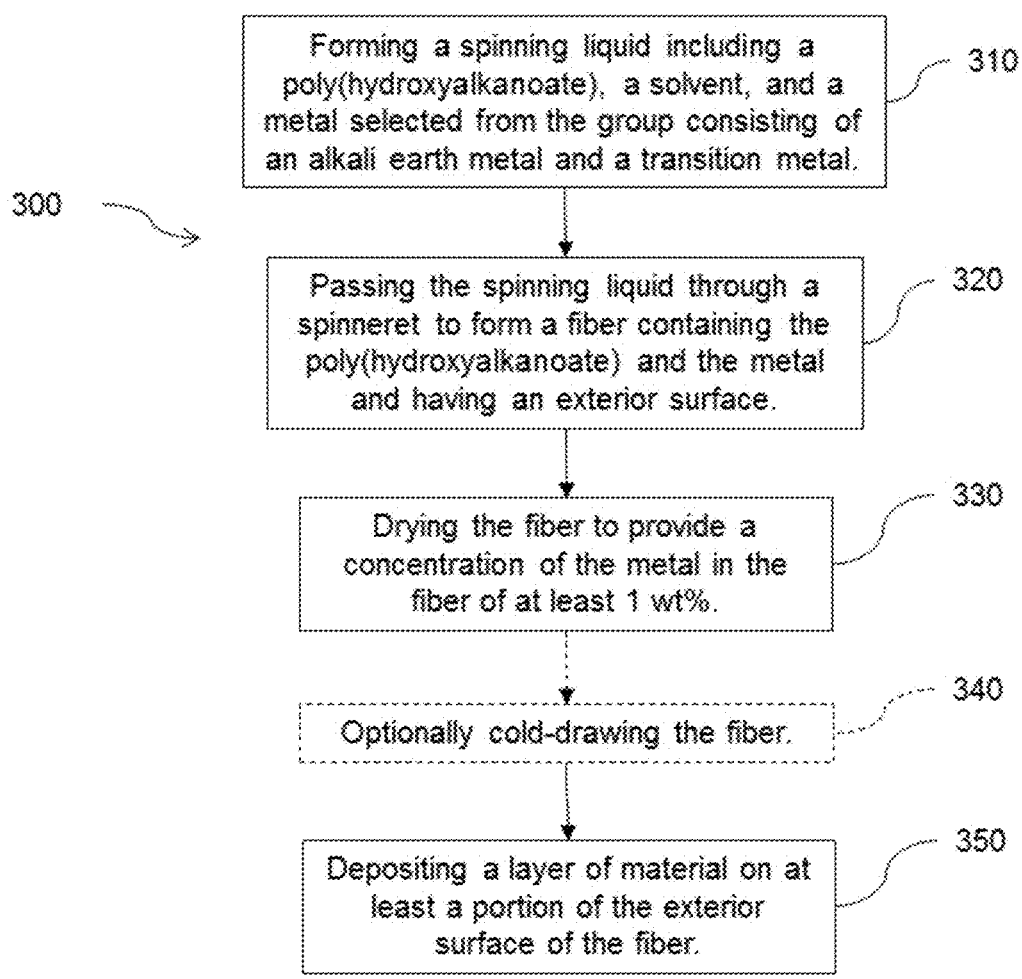
FIG. 3 is a schematic representation of a method of making a partially degradable fiber.

FIG. 3 illustrates a schematic representation of another example of a method of making a partially degradable fiber, such as the partially degradable fiber 100 of FIG. 1. Method 300 includes forming 300 a spinning solution including a poly(hydroxyalkanoate), a solvent, and a metal selected from the group consisting of an alkali earth metal and a transition metal, passing 320 the spinning solution through a spinneret to form a fiber containing the poly(hydroxyalkanoate) and the metal and having an exterior surface, drying 330 the fiber to provide a concentration of the metal in the fiber of at least 0.1 wt %, optionally cold-drawing 340 the fiber, and depositing 350 a layer of a material on at least a portion of the exterior surface of the fiber.

An alkali earth metal or a transition metal may be incorporated into a poly(hydroxyalkanoate) fiber through a liquid spinning process, as outlined by the forming 310, passing 320, drying 330 and optionally cold-drawing 340 of method 300. In one example, a solution of PLA in dichloromethane containing 10% SnOx pbw was spun through a 0.5 millimeter (mm) spinneret to provide a continuous strand of PLA containing the SnOx catalyst. The catalyst-containing fibers formed by liquid spinning converted to gas at a lower temperature and in less time than did comparable fibers formed by an infusion process, as measured by thermogravimetric analysis (TGA), indicating a lower depolymerization onset temperature. Cold-drawing the fibers formed from liquid spinning could increase the fiber strength, ensuring that the fibers can be woven using conventional techniques.

Thermally degradable fibers formed by a liquid spinning process, such as that outlined in FIG. 3, may include a more homogeneous dispersion of catalyst within the fiber than do fibers formed by an infusion process, such as that outlined in FIG. 2. An improvement in catalyst distribution provides for more of the poly(hydroxyalkanoate) polymer to be in close proximity to a catalyst species, which in turn can result in a more efficient depolymerization and a more rapid removal of the fiber. Thermally degradable fibers formed by a liquid spinning process also may reduce the fabrication time for making the fibers, and may reduce the fabrication time for making a microvascular system from the fibers. While an infusion process can be effective in forming thermally degradable fibers, the process can require 24 hours for infusing the catalyst into the fibers, another 24 hours for separating and drying the fibers, and then another 24 hours for degrading and removing the fibers once a composite is formed that includes the fibers as thermally degradable polymeric cores. In contrast, thermally degradable fibers may be formed through liquid spinning within 1 hour, the fibers may be dried within 24 hours, and then the fibers may be degraded and removed from a composite within 2 hours.

A liquid spinning process may be more efficient in its use of catalyst than an infusion process. For example, a spun fiber formed by a liquid spinning process may include a higher concentration of catalyst than an infused fiber formed by an infusion process, even though the spinning liquid and the infusion liquid include the same initial concentration of catalyst. Thus, to achieve a given loading of catalyst in a thermally degradable fiber, a liquid spinning process may require less total catalyst than a comparable infusion process.

Thermally degradable fibers formed by a liquid spinning process may include a wider variety of depolymerization catalysts than can be included using an infusion process. In one example, infusion of PLA fibers with tin(II) octoate (SnOc) provided fibers with a greasy surface, whereas liquid spinning provided PLA fibers containing SnOc, but with a more desirable non-greasy surface. As the depolymerization temperature of PLA fibers containing SnOc is lower than that of PLA fibers containing SnOx, the liquid spinning method can provide PLA fibers that are readily incorporated into a composite and that depolymerize at a relatively low temperature.

A method of making a thermally degradable fiber may include other known methods of incorporating an additive into a polymer fiber, such as melt spinning. In the example of melt spinning, the temperature of the material should be maintained below 180° C., the temperature at which PLA can depolymerize in the presence of a catalyst containing an alkali earth metal or a transition metal. One potential advantage of melt spinning PLA fibers containing a depolymerization catalyst is that the fibers may be stronger than comparable fibers formed by infusion or by liquid spinning.

The depositing (240, 350) a layer of a material on at least a portion of the exterior surface of a fiber may include any of a variety of methods for depositing a coating material on a fiber. The depositing may include contacting the exterior surface of the thermally degradable fiber with a coating precursor, and then solidifying the coating precursor to form a solid coating on at least a portion of the exterior surface of the fiber. A coating precursor may be any substance that can form a solid polymeric material when solidified. The coating precursor may be substantially homogeneous, or it may include other substances, such as fillers and/or viscosity modifiers.

In one example, a coating precursor includes a monomer and/or prepolymer that can polymerize to form a polymer, such as a polymer as described above with regard to coating 120. The coating precursor may then be solidified by polymerizing the monomer and/or prepolymer of the precursor to form the solid polymeric coating. Examples of monomers and/or prepolymers that can polymerize to form a polymer include cyclic olefins; unsaturated monomers such as acrylates, alkylacrylates (including methacrylates and ethacrylates), styrenes, isoprene and butadiene; lactones (such as caprolactone); lactams; epoxy-functionalized monomers, prepolymers or polymers; functionalized siloxanes; and two-part precursors for polymers such as polyethers, polyesters, polycarbonates, polyanhydrides, polyamides, formaldehyde polymers (including phenol-formaldehyde, urea-formaldehyde and melamine-formaldehyde), and polyurethanes. Polymerization of a coating precursor may include crosslinking of monomers and/or prepolymers to form an insoluble polymer network. Crosslinking may be performed by a variety of methods, including the addition of chemical curing agents and/or exposure to radiation such as infrared radiation (IR; i.e. heat), visible light, or ultraviolet radiation (UV).

In another example, the coating precursor includes a polymer in a solvent. The polymer may be dissolved or dispersed in the solvent to form the coating precursor. The coating precursor may be solidified by removing at least a portion of the solvent from the composition to form the solid polymeric coating.

The depositing (240, 350) a layer of a material on at least a portion of the exterior surface of the fiber may further include applying a surface treatment to the solid polymeric coating. Examples of surface treatments include functionalization of the coating by contacting the coating with an oxidizing or reducing atmosphere or by contacting the coating with a liquid containing a functionalizing reagent. Examples of surface treatments include applying an adhesion promoter to the coating.

Figure 4:
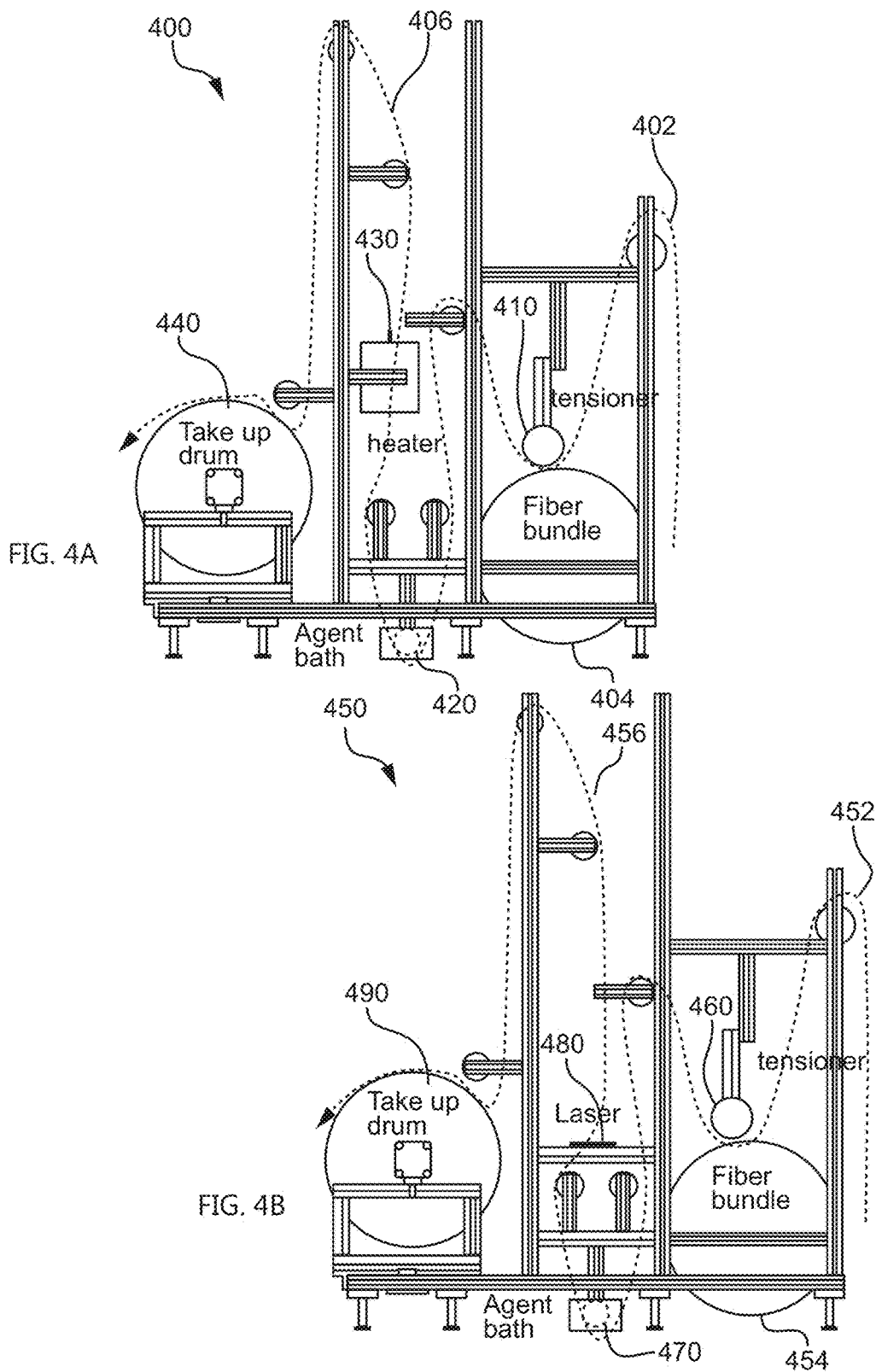
FIGS. 4A and 4B depict examples of an apparatus for depositing a coating on a degradable fiber.

FIG. 4A depicts a schematic representation of an apparatus 400 for depositing a coating on at least a portion of the exterior surface of a thermally degradable fiber. A thermally degradable fiber 402 is unwound from a bundle 404 using a tensioner 410, and then passed through a bath 420 containing a coating precursor. A layer of the precursor is deposited on at least a portion of the exterior surface of the fiber 402 in the bath 420, and the precursor and the fiber are then heated by a heater 430. The precursor on the fiber is solidified due to the heating, providing a coated fiber 406, which is collected on a take-up drum 440. Preferably the coating precursor is solidified at a temperature below the degradation temperature of the thermally degradable fiber 402. The solidification of the coating precursor to form a coating on the fiber may include removal of solvent from the precursor and/or chemical reaction (i.e. curing) of the precursor. Examples of solidification temperatures include 30° C., 50° C., 75° C., 100° C., 125° C., 150° C. and 180° C.

In one example, the coating precursor in the bath 420 includes a mixture of a polyimide in a solvent. When the solvent is removed, the resulting coated fiber 406 includes the thermally degradable fiber 402 and a polyimide coating surrounding at least a portion of the thermally degradable fiber. In another example, the coating precursor in the bath 420 includes a mixture of a polyimide and a thermally degradable poly(hydroxyalkanoate) such as PLA in a solvent. When the solvent is removed, the resulting coated fiber 406 includes the thermally degradable fiber 402 and a coating containing both a polyimide and the poly(hydroxyalkanoate), surrounding at least a portion of the thermally degradable fiber.

FIG. 4B depicts a schematic representation of an apparatus 450 for depositing a coating on at least a portion of the exterior surface of a thermally degradable fiber. A thermally degradable fiber 452 is unwound from a bundle 454 using a tensioner 460, and then passed through a bath 470 containing a coating precursor. A layer of the precursor is deposited on at least a portion of the exterior surface of the fiber 452 in the bath 470, and the precursor and the fiber is then irradiated by a radiation source 480. The precursor on the fiber is cured due to the irradiation, providing a coated fiber 456, which is collected on a take-up drum 490. Preferably the irradiation does not cause degradation of the thermally degradable fiber 452.

In one example, the coating precursor in the bath 470 includes a mixture of a polysiloxane precursor and an ultraviolet (UV) initiator in a solvent. When the polysiloxane is cured, the resulting coated fiber 456 includes the thermally degradable fiber 452 and a polysiloxane coating surrounding at least a portion of the thermally degradable fiber.

Composite Materials Including Partially Degradable Polymeric Fibers

Figure 5:
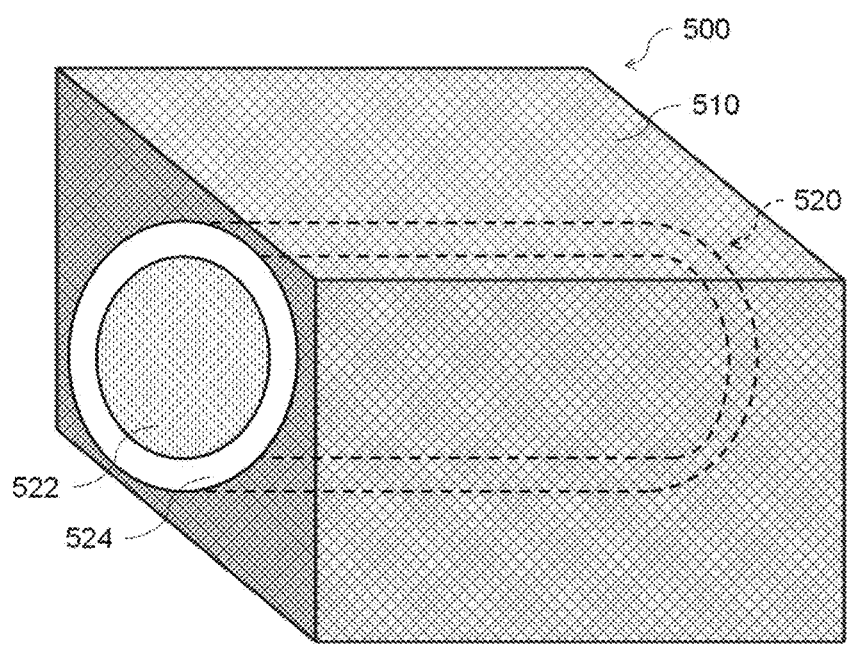
FIG. 5 depicts a composite material containing a partially degradable polymeric fiber.

FIG. 5 depicts a schematic representation of a composite material 500 that includes a solid polymeric matrix 510 and a partially degradable fiber 520 in the polymeric matrix. The solid polymeric matrix 510 includes a first material. The partially degradable fiber 520 includes a thermally degradable polymeric core 522 and a coating 524 surrounding at least a portion of the core. The coating 524 includes a second material, which is different from the first material of the matrix 510.

The solid polymer matrix 510 may include a polyamide such as nylon; a polyester such as poly(ethylene terephthalate) and polycaprolactone; a polycarbonate; a polyether; an epoxy polymer; an epoxy vinyl ester polymer; a polyimide such as polypyromellitimide (for example KAPTON®); a phenol-formaldehyde polymer such as bakelite; an amine-formaldehyde polymer such as a melamine polymer; a polysulfone; a poly(acrylonitrile-butadiene-styrene) (ABS); a polyurethane; a polyolefin such as polyethylene, polystyrene, polyacrylonitrile, a polyvinyl, polyvinyl chloride and poly(DCPD); a polyacrylate such as poly(ethyl acrylate); a poly(alkylacrylate) such as poly(methyl methacrylate); a polysilane such as poly(carborane-silane); and/or a polyphosphazene.

The solid polymer matrix 510 may include an elastomer, such as an elastomeric polymer, an elastomeric copolymer, an elastomeric block copolymer, and/or an elastomeric polymer blend. Examples of elastomer polymers include polyolefins, polysiloxanes such as poly(dimethylsiloxane) (PDMS), polychloroprene, and polysulfides; examples of copolymer elastomers may include polyolefin copolymers and fluorocarbon elastomers; examples of block copolymer elastomers may include acrylonitrile block copolymers, polystyrene block copolymers, polyolefin block copolymers, polyester block copolymers, polyamide block copolymers, and polyurethane block copolymers; and examples of polymer blend elastomers include mixtures of an elastomer with another polymer. Composite materials that include an elastomer as the solid polymer matrix are disclosed, for example, in U.S. Pat. No. 7,569,625 to Keller et al., and in U.S. Application Publication 2009/0191402 to Beiermann et al., which are incorporated by reference. The solid polymer matrix 510 may include a mixture of these polymers, including copolymers that include repeating units of two or more of these polymers, and/or including blends of two or more of these polymers.

The solid polymer matrix 510 may include other ingredients in addition to the polymeric material. For example, the matrix may contain one or more particulate fillers, stabilizers, antioxidants, flame retardants, plasticizers, colorants and dyes, fragrances, or adhesion promoters. An adhesion promoter is a substance that increases the adhesion between two substances, such as the adhesion between two polymers. One type of adhesion promoter that may be present includes substances that promote adhesion between the solid polymer matrix 510 and the coating 524.

The partially degradable fiber 520, including the thermally degradable polymeric core 522 and the coating 524 surrounding at least a portion of the core, may be as described above for the partially degradable fiber 100. The partially degradable fiber 520 may be configured in a variety of shapes, including a woven shape. In one example, composite 500 includes a woven structure in the solid polymer matrix 510, where the woven structure includes a plurality of partially degradable fibers 520 that are interwoven. In another example, composite 500 includes a woven structure in the solid polymer matrix 510, where the woven structure includes a first plurality of partially degradable fibers, and a second plurality of partially degradable fibers. In this example, each plurality of partially degradable fibers may be as described above for the partially degradable fiber 520. In yet another example, composite 500 includes a woven structure in the solid polymer matrix 510, where the woven structure includes a plurality of partially degradable fibers 520, and a plurality of reinforcing fibers.

When the composite 500 is heated to and maintained at a temperature of from 100 to 250° C., the thermally degradable polymeric core 522 can form degradants that can be removed from the composite 500. Complete degradation of the core 522 and removal of the resulting degradants yields a microvascular system containing the solid polymeric matrix 510 and a microfluidic channel, where the walls of the microfluidic channel are provided by the coating 524.

Microvascular Systems Formed from Partially Degradable Polymeric Fibers

Figure 6:
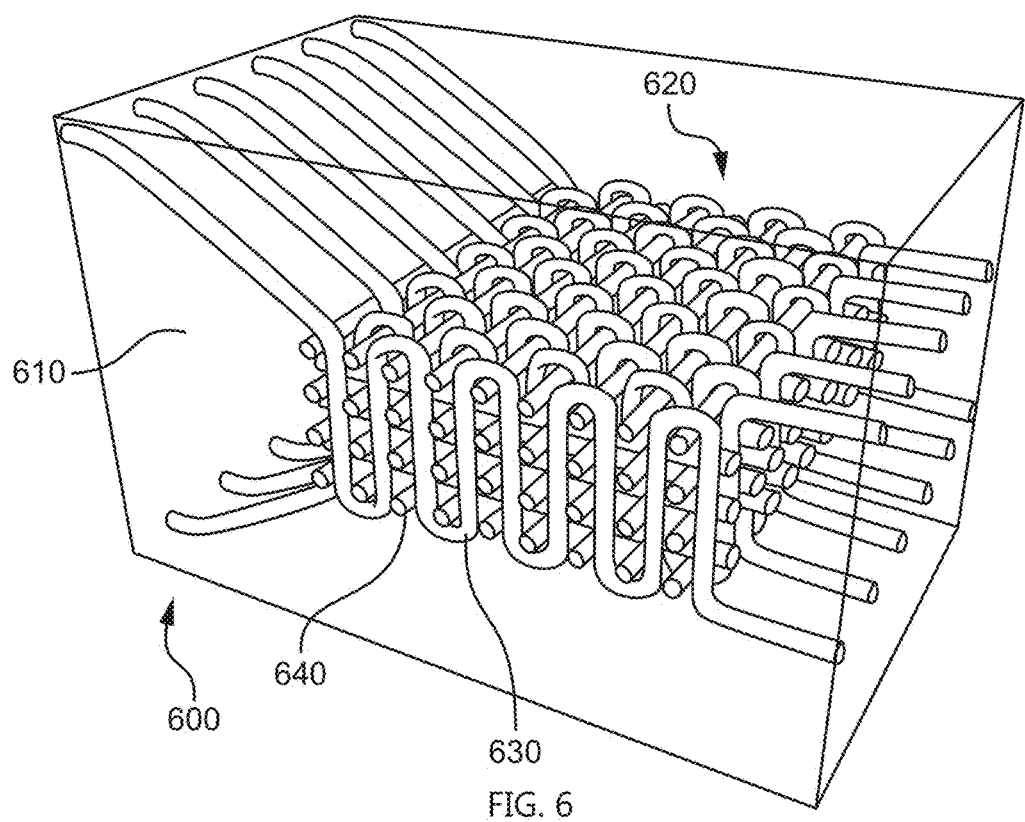
FIG. 6 depicts a microvascular system.

FIG. 6 depicts a schematic representation of a microvascular system 600, which includes a solid polymeric matrix 610 and a woven structure 620 in the matrix. The woven structure 620 includes at least one ply containing a plurality of microfluidic channels 630. The microfluidic channels 630 have a channel wall including a material that is different from the material of the solid polymeric matrix 610. The woven structure 620 optionally includes a plurality of structures 640, which may include a plurality of fibers and/or a second plurality of microfluidic channels.

The woven structure 620 includes at least one ply containing at least one plurality of microfluidic channels 630, and may include more than one ply containing microfluidic channels. For a microvascular system that includes the optional second plurality of microfluidic channels (i.e. 640), the woven structure 620 also may include at least one ply containing only the first plurality of microfluidic channels 630 and/or may include at least one ply containing only the second plurality of microfluidic channels 640. Each plurality of microfluidic channels has channel walls including materials that are different from the material of the solid polymeric matrix 610.

The microfluidic channels 630 may include a fluid, such as a gas or a liquid, or they may include a vacuum. The microvascular system 600 may be referred to as an "apomatrix" when the microfluidic channels 630 include a fluid. Without fluid, or with air, microvascular system 600 may be referred to as a "holomatrix".

A variety of fluids may be present in the microfluidic channels of a microvascular system such as system 600, including aqueous solutions, organic solvents, liquid metals, reactive gases and inert gases. A fluid in the microfluidic channels 630 can flow through one channel and into another channel by way of an interconnect between the channels. An interconnect is present wherever two or more channels are in contact without a channel wall separating the channels. In this manner, interconnects establish fluid communication between the channels. Microfluidic channels 630 that are interconnected thus form a microfluidic network. If the polymeric matrix includes an inlet port, a fluid delivered through the inlet port can flow through interconnected microfluidic channels 630 within the polymeric matrix. If the interconnected microfluidic channels form a network, the introduced fluid may at least partially fill the network.

For a microvascular system that includes the optional second plurality of microfluidic channels (i.e. 640), the first plurality of microfluidic channels 630 and the second plurality of microfluidic channels 640 may be independent, or they may be in fluid communication. Fluid communication between the first and second pluralities of microfluidic channels may be provided by interconnects between channels. Fluid communication between the first and second pluralities of microfluidic channels also may be provided by channels that are in contact, even if the channels are separated by one or more channel walls. The latter type of fluid communication is provided by permeation of a fluid through the channel wall(s).

The nature and/or level of any fluid communication between the first and second plurality of microfluidic channels is affected by the relative configurations of the microfluidic channels. For a first and second plurality of channels that are in fluid communication, it is preferred that at least one channel of each of the pluralities are in physical contact with each other. If the channels are not in physical contact, fluid communication would require permeation of a fluid through the solid polymer matrix, in addition to permeation through the channel wall(s).

The nature and/or level of any fluid permeation between the first and second plurality of microfluidic channels is affected by the properties of their channel walls. In one example, the channel walls of the microfluidic channels 630 are impermeable to a fluid within the channels. An impermeable channel wall may allow substantially no transport of a liquid through the channel wall. For example, the channel wall may include a liquid barrier polymer such as polyethylene, polypropylene, polystyrene, polyamide, polyester, polycarbonate (PC), poly(methyl methacrylate) (PMMA), or poly(vinyl chloride) (PVC). An impermeable channel wall may allow substantially no transport of a gas through the channel wall. For example, the channel wall may include a gas barrier polymer such as isobutylene-isoprene rubber, bromobutyl rubber, chlorobutyl rubber, or poly(tetrafluoroethylene) (PTFE) or other fluoroelastomers.

In another example, the channel walls of the microfluidic channels 630 are permeable to a fluid within the channels. A permeable channel wall may allow a liquid and/or a gas to be transported through the channel wall. For example, the channel wall may include a porous polymeric material conventionally used for ultrafiltration membranes, microfiltration membranes, nanofiltration membranes, or reverse osmosis membranes. Such porous materials may be formed from polymers such as cellulose acetate, polyethylene, polypropylene, PVC, polysulfone, polyamide, polyimide, polysulfone, polyether sulfone, poly(vinylidene fluoride) (PVDF), polyacrylonitrile (PAN), and ion-exchange membrane such as a sulfonated PTFE (for example NAFION® (DuPont)).

The permeability properties of a channel wall material may depend on the chemical nature of the fluid. A channel wall is semi-permeable when it is permeable to some fluids, but impermeable to other fluids. For example, a hydrophobic polymer may be impermeable with regard to aqueous liquids, but may have some permeability with regard to lipophilic liquids such as hydrocarbons. Examples of hydrophobic polymers include polyethylene, polypropylene, PVC, polysulfone, and PTFE. In another example, a hydrophilic polymer may be impermeable with regard to lipophilic liquids, but may have some permeability with regard to aqueous liquids. Examples of hydrophilic polymers include cellulose polymers and poly(vinyl alcohol).

As noted above, the woven structure 620 includes at least one ply containing at least one plurality of microfluidic channels 630. The woven structure 620 may include more than one ply containing microfluidic channels. For a microvascular system that includes the optional fibers (i.e. 640), the woven structure 620 also may include at least one ply containing a plurality of fibers without any microfluidic channels and/or may include at least one ply containing a plurality of microfluidic channels 630 without any fibers. The fibers may be present as tows, also referred to as yarns, which are assemblies of from 100 to 12,000 individual fibers.

Optional fibers (i.e. 640) may include a material having an aspect ratio (diameter:length) of at least 1:10, including at least 1:100 and at least 1:1,000. If present, the optional fibers preferably include reinforcing fibers that, when added to a solid polymer matrix, increase the strength of the matrix relative to the pure polymer. Reinforcing fibers may include an inorganic and/or an organic material. Examples of fibrous reinforcing materials include graphite fibers, ceramic fibers, metal fibers, and polymer fibers. Examples of graphite reinforcing fibers include THORNEL® 25 (Cytec, Tempe, Ariz.) and MODMOR® (Morganite, United Kingdom). Examples of ceramic reinforcing fibers include metal oxide fibers such as titanium oxide fibers, zirconium oxide fibers and aluminum oxide fibers; silica fibers; and glass fibers, such as E-glass fibers and S-glass fibers. Examples of metal fibers include steel fibers, tungsten fibers, beryllium fibers, and fibers containing alloys of these metals. Examples of polymer fibers include polyester fibers, nylon fibers, rayon fibers, and polyaramid fibers, such as KEVLAR® 49 (DuPont).

The woven structure 620 may be a two-dimensional (2D) structure, in which the ply includes threads oriented in two different directions in substantially a single plane. The woven structure 620 may be a three-dimensional (3D) structure, in which the ply includes threads oriented in two different directions in substantially a single plane, and further includes threads oriented in a third direction that is substantially orthogonal to the plane. An individual "thread" in the woven structure 620 may be a microfluidic channel 630 or a structure 640, which may be an individual fiber, a fiber tow, or a microfluidic channel of a second plurality of channels.

The microfluidic channels 630 (and optionally 640) may include substantially tubular channels having a diameter less than 1,000 micrometers. The term "substantially tubular" means that the majority of the cross-sectional periphery of the channel through the substrate matrix is curved in shape. Curved can include circular, elliptic, rounded, arched, parabolic and other curved shapes. The average diameter of the substantially tubular channels preferably is from 0.1 to 1,000 micrometers, from 10 to 750 micrometers, from 20 to 500 micrometers, or from 50 to 250 micrometers. The microfluidic channels 630 may have a length of at least 1 centimeter.

At least a portion of the microfluidic channels 630 can be independent, existing in the matrix 610 without any interconnect with another channel. In one example, all of the microfluidic channels 630 in a microvascular system 600 are independent, and the system does not include a microfluidic network. In this example, any fluid in an individual microfluidic channel 630 is not in fluid communication with a fluid in another microfluidic channel.

The microfluidic channels 630 in the polymeric matrix 610 can affect the structural properties of the matrix, and the type and magnitude of the resulting structural property changes may depend on the properties of the channels and their configuration in the matrix. For example, it may be desirable for the microfluidic channels 630 to have a minimum channel spacing and a maximum channel diameter, which may help to minimize any decrease in the strength of the matrix.

Figure 7:
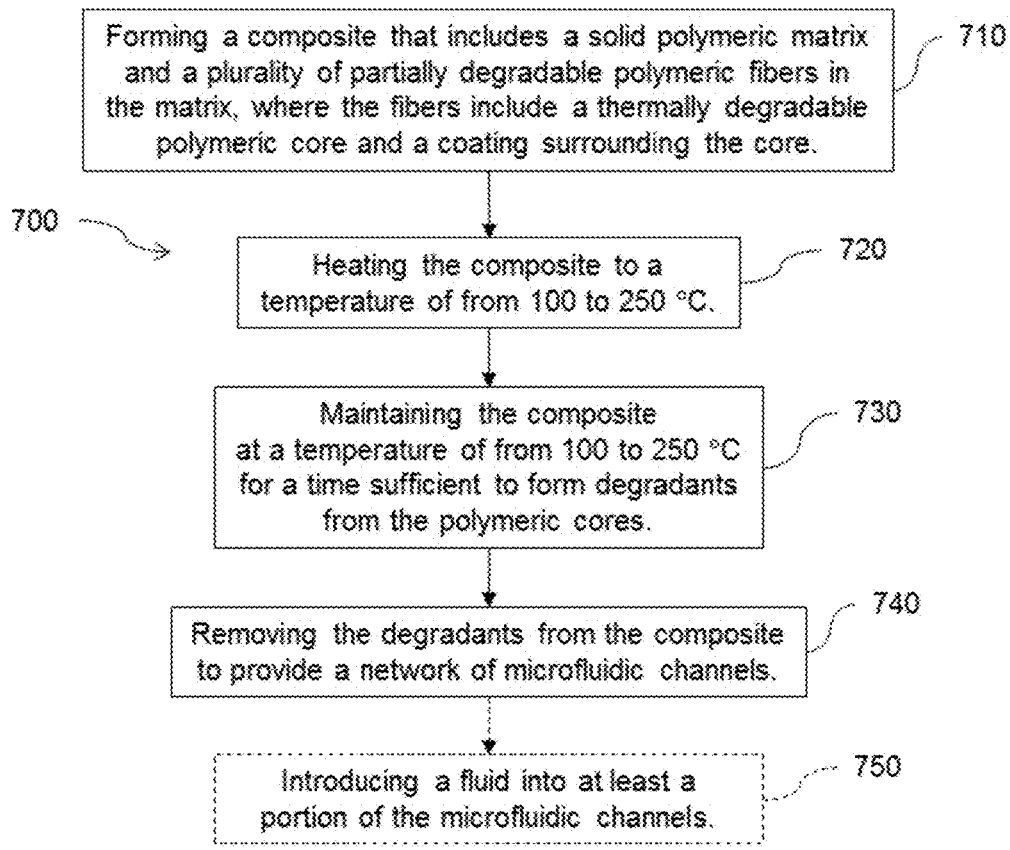
FIG. 7 is a schematic representation of a method of making a microvascular system.

Methods of Making a Microvascular System from Partially Degradable Polymeric Fibers FIG. 7 illustrates a schematic representation of an example of a method of making a microvascular system.

Method 700 includes forming 710 a composite that includes a solid polymeric matrix and a plurality of partially degradable fibers in the matrix, where the partially degradable fibers include a thermally degradable polymeric core and a coating surrounding the core. Method 700 further includes heating 720 the composite to a temperature of from 100 to 250° C., maintaining 730 the composite at a temperature of from 100 to 250° C. for a time sufficient to form degradants from the polymeric cores, and removing 740 the degradants from the composite to provide microfluidic channels. Method 700 optionally further includes introducing 750 a fluid into at least a portion of the microfluidic channels.

Forming 710 a composite that includes a solid polymeric matrix and a plurality of partially degradable polymeric fibers in the matrix may include combining a matrix precursor with a plurality of partially degradable polymeric fibers, and then solidifying the matrix precursor to form a solid polymer matrix. The method may further include forming the partially degradable polymeric fibers and/or the matrix precursor.

The matrix precursor may be any substance that can form a solid polymer matrix when solidified. The matrix precursor may be substantially homogeneous, or it may include other substances, such as fillers and/or viscosity modifiers. For example, a matrix precursor may include particles that can change the viscosity of the precursor and/or can change the properties of the polymeric matrix formed from the precursor. Examples of particles that may be present in the matrix precursor include plastic particles and non-plastic particles, such as ceramics, glasses, semiconductors, and metals.

In one example, the matrix precursor includes a monomer and/or prepolymer that can polymerize to form a polymer. The sacrificial fibers and optionally other ingredients may be mixed with the monomer or prepolymer. The matrix precursor may then be solidified by polymerizing the monomer and/or prepolymer of the matrix precursor to form the solid polymer matrix.

Examples of monomers and/or prepolymers that can polymerize to form a polymer include cyclic olefins; unsaturated monomers such as acrylates, alkylacrylates (including methacrylates and ethacrylates), styrenes, isoprene and butadiene; lactones (such as caprolactone); lactams; epoxy-functionalized monomers, prepolymers or polymers; functionalized siloxanes; and two-part precursors for polymers such as polyethers, polyesters, polycarbonates, polyanhydrides, polyamides, formaldehyde polymers (including phenol-formaldehyde, urea-formaldehyde and melamine-formaldehyde), and polyurethanes. Polymerization of a matrix precursor may include crosslinking of monomers and/or prepolymers to form an insoluble polymer network. Crosslinking may be performed by a variety of methods, including the addition of chemical curing agents, exposure to light or other forms of radiation, or heating. If a chemical curing agent is used, it may be added to the matrix precursor before or after it is combined with the sacrificial fibers.

In another example, the matrix precursor includes a polymer in a matrix solvent. The polymer may be dissolved or dispersed in the matrix solvent to form the matrix precursor, and the sacrificial fibers and optionally other ingredients then mixed into the matrix precursor. The matrix precursor may be solidified by removing at least a portion of the matrix solvent from the composition to form the solid polymer matrix.

In another example, the matrix precursor includes a polymer that is at a temperature above its melting temperature. The polymer may be melted to form the matrix precursor and then mixed with the sacrificial fibers and optionally other ingredients. The matrix precursor may be solidified by cooling the composition to a temperature below the melt temperature of the polymer to form the solid polymer matrix.

Forming 710 preferably includes contacting the partially degradable polymeric fibers with a matrix precursor at a temperature below the degradation temperature of the thermally degradable polymeric core. Preferably the partially degradable polymeric fibers are contacted with a matrix precursor at a temperature between 30° C. and 250° C., including temperatures between 50° C. and 200° C., between 75° C. and 175° C., and between 100° C. and 150° C. In one example, forming 710 includes contacting the partially degradable polymeric fibers with a matrix precursor that includes a monomer and/or prepolymer, and heating the matrix precursor and the partially degradable polymeric fibers for a time sufficient to polymerize the monomer and/or prepolymer. In another example, forming 710 includes contacting the partially degradable polymeric fibers with a matrix precursor that includes a polymer that is at a temperature above its melting temperature.

The partially degradable fibers include a thermally degradable polymeric core having a degradation temperature of at most 250° C., and a coating surrounding at least a portion of the core, where at least a portion of the coating does not thermally degrade at temperatures below 275° C. The partially degradable fibers may be as described above for partially degradable fiber 100.

Heating 720 the composite to a temperature of from 100 to 250° C. and maintaining 730 the composite at a temperature of from 100 to 250° C. for a time sufficient to form degradants from the thermally degradable polymeric cores of the partially degradable polymeric fibers may include, for example, placing the composite in an oven. The degradants preferably have an average molecular weight less than 500 Daltons, and preferably are in a gas phase.

Removing 740 the degradants from the composite may include contacting at least a portion of a surface of the composite with a vacuum source. Removing 740 the degradants from the composite may include contacting at least a portion of a surface of the composite with a pressurized fluid, such as a gas. Use of a pressurized fluid or a vacuum may facilitate removal of gaseous degradants. The composite may be maintained at a temperature of from 100 to 250° C. during the removal, or the temperature of the composite may be raised or lowered prior to or during the removal. Removing 740 the degradants from the composite may occur simultaneously with the heating 720 and/or maintaining 730 of the composite, or the removing may occur after the maintaining 730 of the composite.

Optionally introducing 750 a fluid into at least a portion of the microfluidic channels may include any of a variety of methods for introducing a fluid into a microfluidic channel. In one example, the fluid may be injected into one or more channels. In another example, one or more channel openings may be placed in contact with a reservoir of the fluid. The fluid may then flow through the channels through capillary action.

Figure 8:
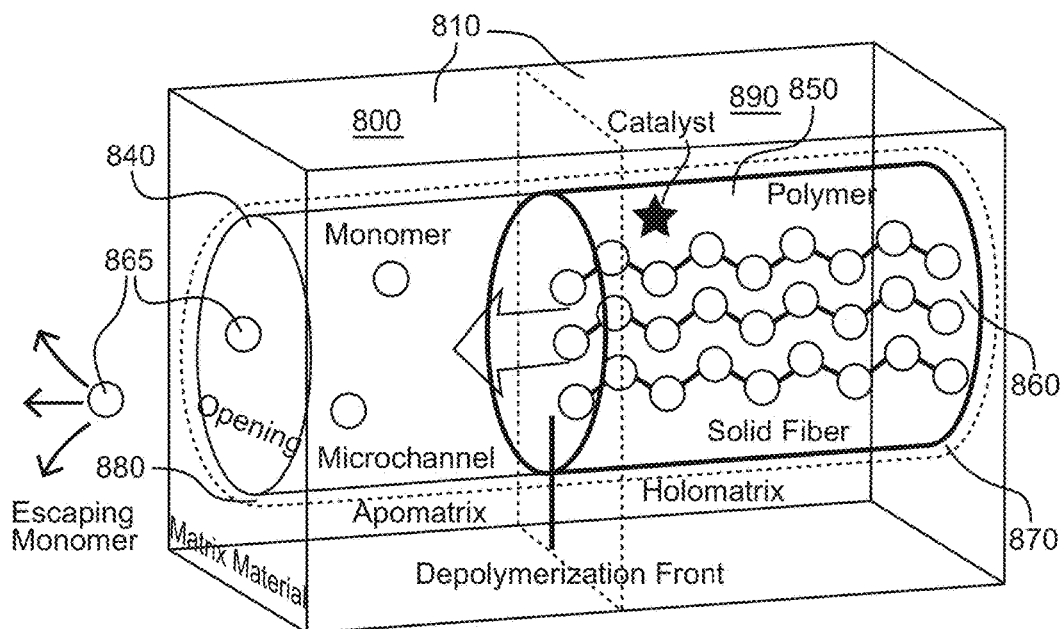
FIG. 8 illustrates the formation of a microvascular system from a composite material containing a partially degradable polymeric fiber.

FIG. 8 depicts a schematic representation of a composite 890, which includes a solid polymeric matrix 810 and a plurality of partially degradable fibers 850, and of a composite 800, which includes the polymeric matrix 810 and a plurality of microfluidic channels 840. The partially degradable fiber 850 includes a thermally degradable polymeric core 860 and a coating 870 surrounding at least a portion of the core. In FIG. 8, the thermally degradable polymeric core 860 is being converted into degradants 865 that are subsequently removed, forming the microfluidic channel 840 having wall 880 provided by the coating 870. Composite 890 may be the product of the forming 710 of method 700 of FIG. 7, for example. Composite 800 may be the product of the heating 720, maintaining 730 and removing 740 of method 700 of FIG. 7, for example.

The solid polymer matrix 810 may include a polymeric material, and may include other ingredients in addition to the polymeric material, as described above for solid polymer matrix 510 of FIG. 5. The microfluidic channels 540 may have the dimensions and configuration as described above for microfluidic channels 540.

The partially degradable fiber 850 should be strong enough to survive a mechanical weaving process to survive being combined with a matrix precursor. The partially degradable fiber 850 also should remain solid during solidification of the matrix precursor into a polymeric matrix. For solidification by polymerization and/or curing, the partially degradable fiber 850 preferably should remain solid at temperatures up to 180° C. The thermally degradable polymeric core 860 of the partially degradable fiber 850 also should be easily removed from a polymeric matrix by degradation to volatile degradants at higher temperatures. The thermally degradable polymeric core 860 also should have degradation and volatilization temperatures within a narrow range between the highest matrix solidification temperatures and the lowest thermal degradation temperatures of the polymeric matrix (200-240° C.). Preferably, the degradation temperature of the thermally degradable polymeric core 860 is at most 250° C. More preferably, the degradation temperature of the core is at most 220° C., and more preferably is at most 180° C.

Figure 9:
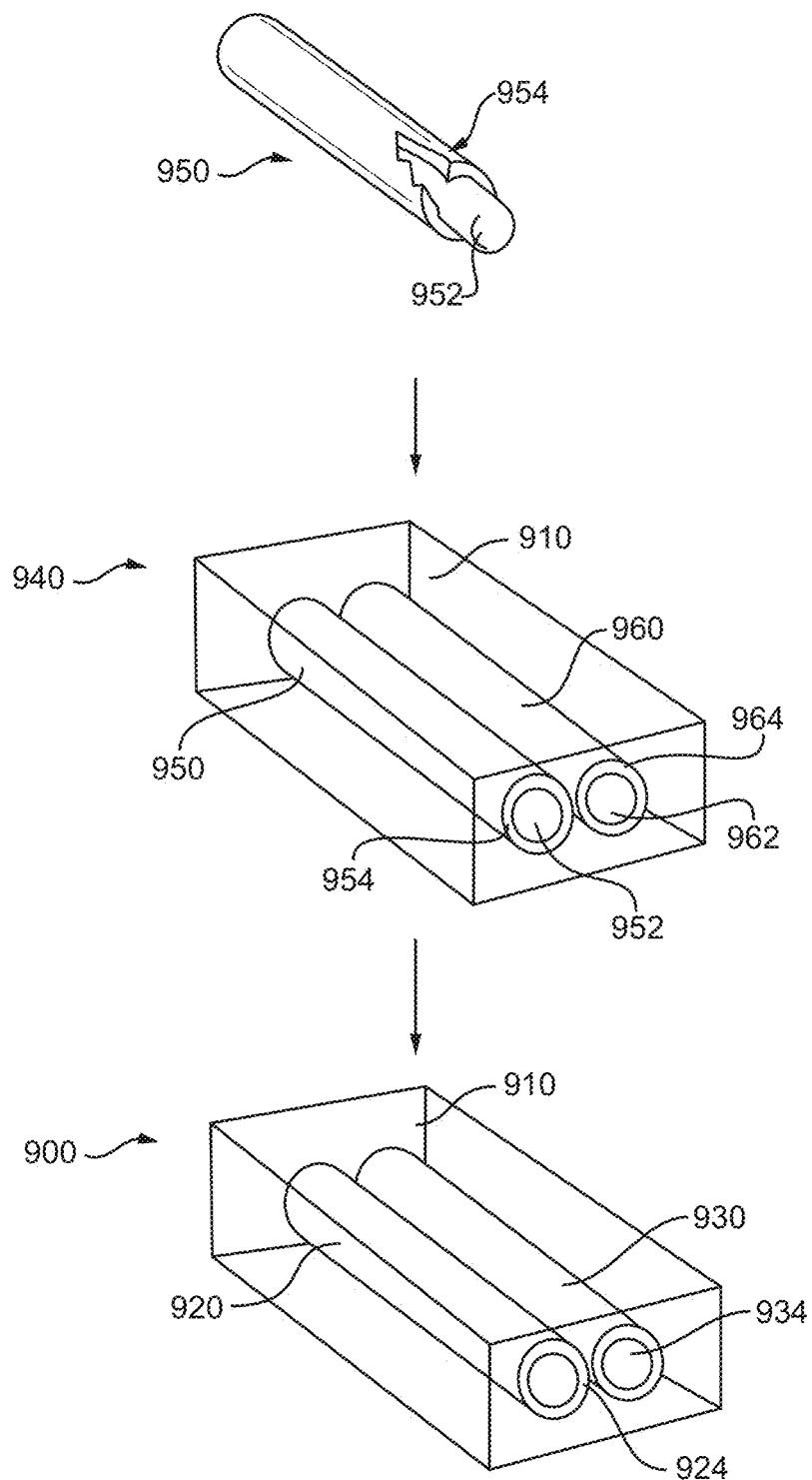
FIG. 9 illustrates the formation of a microvascular system having two microchannels, from a composite material containing two partially degradable polymeric fibers.

FIG. 9 depicts a schematic representation of a microvascular system 900, which includes a solid polymeric matrix 910, a first microfluidic channel 920 in the solid polymeric matrix, and a second microfluidic channel 930 in the solid polymeric matrix. The first microfluidic channel 920 has a first channel wall 924 including a polymer that is different from the solid polymeric matrix 910, and the second microfluidic channel 930 has a second channel wall 934 including a polymer that is different from the solid polymeric matrix 910.

The first channel 920 may include a first fluid, and the second channel 930 may include a second fluid different from the first fluid. As channels 920 and 930 are in physical contact, the level of communication between the first and second fluids is determined by the permeabilities of the channel walls 924 and 934. If both channel walls are permeable to both fluids, then the first and second fluids can combine, forming a mixture of the fluids in each channel. If both channel walls are permeable only to the first fluid and/or to an ingredient of the first fluid, then the first fluid may permeate through the channel walls and combine with the second fluid. In this example, the second channel 930 can contain a mixture of the first and second fluids, while the first channel 920 is depleted of the first fluid and/or maintains the first fluid at a reduced fluid pressure. If both channel walls are impermeable to both fluids, then the first and second fluids can flow through their respective microfluidic channels without mixing with each other. The first and second channel walls 924 and 934 may include the same polymer, or they may include different polymers.

The microvascular system 900 may be formed from a composite material 940 including the solid polymeric matrix 910, a first partially degradable fiber 950 in the solid polymeric matrix, and a second partially degradable fiber 960 in the solid polymeric matrix. The first partially degradable fiber 950 includes a first thermally degradable polymeric core 952 and a first coating 954 surrounding at least a portion of the core. The second partially degradable fiber 960 includes a second thermally degradable polymeric core 962 and a first coating 964 surrounding at least a portion of the core. The microvascular system 900 may be formed from the composite material 940 by heating the composite to a temperature of from 100 to 250° C., maintaining the composite at a temperature of from 100 to 250° C. for a time sufficient to form degradants from the thermally degradable polymeric cores 952 and 962, and removing the degradants from the composite to provide microfluidic channels 920 and 930.

The first and second thermally degradable polymeric cores 952 and 962 may include the same polymer, or they may include different polymers. Preferably the first and second cores are the same material, as this can provide for removal of both cores simultaneously. The first and second coatings 924 and 934 may include the same polymer, or they may include different polymers.

The composite material 940 may be formed by placing the first partially degradable fiber 950 and the second partially degradable fiber 960 in a desired configuration, contacting the fibers with a matrix precursor, and solidifying the matrix precursor to form the polymeric matrix 910. The partially degradable fibers (i.e. 950) may be formed by depositing a coating 954 on at least a portion of an external surface of a thermally degradable polymeric fiber 952.

Figure 10:
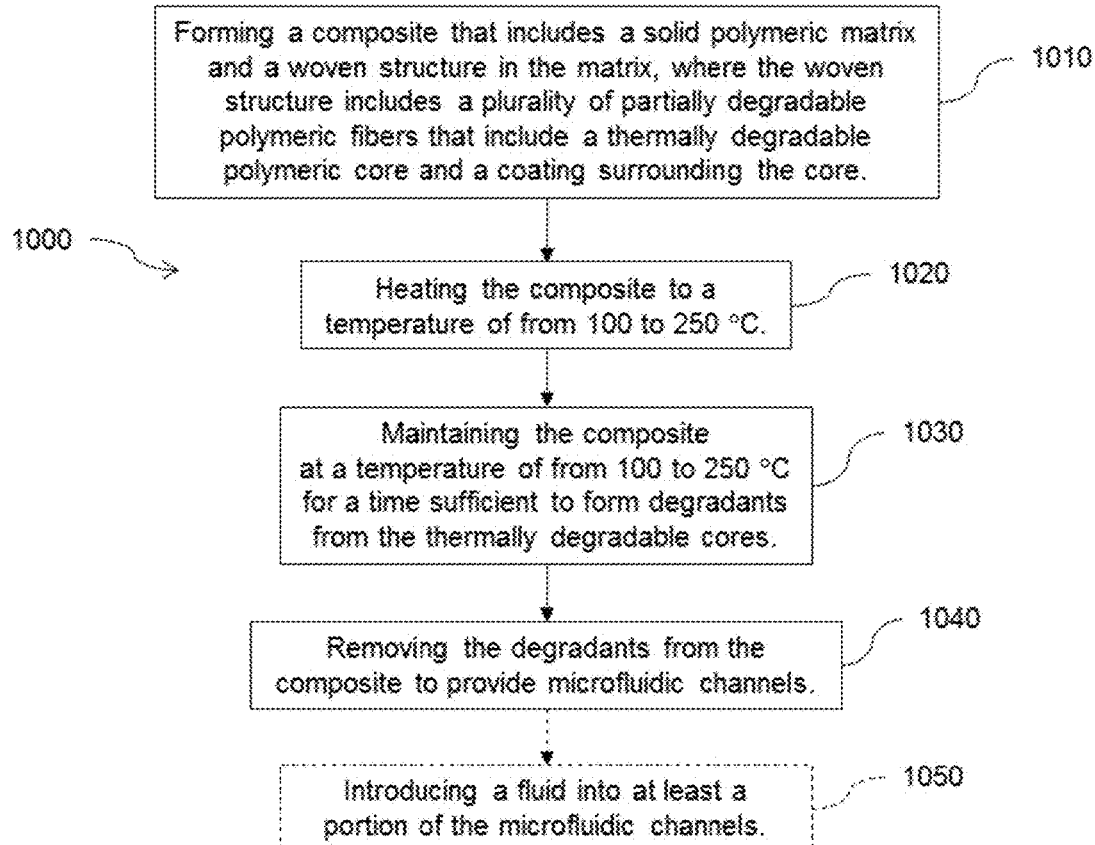
FIG. 10 is a schematic representation of a method of making a microvascular system.

FIG. 10 illustrates a schematic representation of an example of a method of making a microvascular system, such as microvascular system 600 of FIG. 6 or microvascular system 900 of FIG. 9. Method 1000 includes forming 1010 a composite that includes a solid polymeric matrix and a woven structure in the matrix, where the woven structure includes a plurality of partially degradable polymeric fibers. The partially degradable fibers include a thermally degradable polymeric core, and a coating surrounding at least a portion of the core. Method 1000 further includes heating 1020 the composite to a temperature of from 100 to 250° C., maintaining 1030 the composite at a temperature of from 100 to 250° C. for a time sufficient to form degradants from the thermally degradable polymeric cores, and removing 1040 the degradants from the composite to provide microfluidic channels. The degradants preferably have an average molecular weight less than 500 Daltons. Method 1000 optionally further includes introducing 1050 a fluid into at least a portion of the microfluidic channels.

Forming 1010 a composite that includes a solid polymeric matrix and a woven structure in the matrix may include combining a matrix precursor with the partially degradable polymeric fibers, and then solidifying the matrix precursor to form a solid polymer matrix. The method may further include forming the partially degradable polymeric fibers and/or the matrix precursor.

Forming 1010 may include forming the woven structure by weaving the plurality of partially degradable polymeric fibers to form a single ply. In one example, an arrangement of warp threads in a first orientation may be held in tension, and weft threads then may be directed sinusoidally in a second orientation through the warp threads. Preferably the second direction is transverse to the first orientation. In this example, the resulting ply is a 2D woven structure.

In another example, an arrangement of warp threads in a first orientation may be held in tension. Weft threads then may be directed in a second orientation over, under and/or through the warp threads, where the second direction preferably is transverse to the first orientation. Z-threads then may be directed through the warp and weft threads, preferably in an orientation that is orthogonal to a plane formed by the weft and warp threads. The Z-threads may be directed through the weft and warp threads sinusoidally. The warp, weft and/or Z-threads may include partially degradable polymeric fibers. In this example, the resulting ply is a 3D woven structure.

Forming 1010 may include forming the woven structure by weaving the plurality of partially degradable polymeric fibers with a second plurality of partially degradable polymeric fibers and/or with reinforcing fibers to form a single ply. In one example, the warp threads may include the plurality of partially degradable polymeric fibers, and the weft threads may include a second plurality of partially degradable polymeric fibers and/or reinforcing fibers. In another example, the warp threads may include a second plurality of partially degradable polymeric fibers and/or reinforcing fibers, and the weft threads may include the plurality of partially degradable polymeric fibers. In these examples, the resulting plies are 2D woven structures.

In another example, an arrangement of warp threads in a first orientation may be held in tension, weft threads then may be directed in a second orientation over, under and/or through the warp threads, where the second direction preferably is transverse to the first orientation, and Z-threads then may be directed through the warp and weft threads, preferably in an orientation that is orthogonal to a plane formed by the weft and warp threads. The Z-threads may be directed through the weft and warp threads sinusoidally. At least one of the warp, weft and/or Z-threads may include the partially degradable polymeric fibers, and the remaining threads may include a second plurality of partially degradable polymeric fibers and/or reinforcing fibers. In this example, the resulting ply is a 3D woven structure.

Forming 1010 may include inserting the plurality of partially degradable polymeric fibers into a ply of woven a second plurality of partially degradable polymeric fibers and/or reinforcing fibers. In one example, a partially degradable polymeric fiber is stitched into a woven ply of fibers, such as by repeatedly piercing the ply with a needle attached to a partially degradable polymeric fiber, and forming a sinusoidal trace of the partially degradable polymeric fiber that traverses the thickness of the ply. In this example, a pattern of the first plurality of partially degradable polymeric fibers may be formed along the length and width of the woven ply.

In one example, the plurality of partially degradable polymeric fibers and a second plurality of partially degradable polymeric fibers and/or reinforcing fibers may be arranged into two- or three-dimensional woven preforms. The position, length, diameter, and curvature of the partially degradable polymeric fibers and/or reinforcing fibers may be varied to meet desired design criteria.

Forming 1010 includes combining the partially degradable polymeric fibers and a matrix precursor. The matrix precursor may be as described with regard to forming 710 of FIG. 7. Forming 1010 preferably includes contacting the partially degradable polymeric fibers with a matrix precursor and heating the matrix precursor to a temperature of at least 75° C. for a time sufficient to form the polymeric matrix. In one example, forming 1010 includes infiltrating the interstitial pore space between fibers with a low-viscosity thermosetting resin (e.g. epoxy) and curing at elevated temperature. After curing, the sample may be trimmed to expose the ends of the partially degradable polymeric fibers.

Heating 1020 the composite to a temperature of from 100 to 250° C. and maintaining 1030 the composite at a temperature of from 100 to 250° C. for a time sufficient to form degradants from the thermally degradable polymeric cores may include, for example, placing the composite in an oven. The degradants preferably have an average molecular weight less than 500 Daltons, and preferably are in a gas phase. Removing 1040 the degradants from the composite may include contacting at least a portion of a surface of the composite with a vacuum source or with a pressurized fluid. The heating 1020, maintaining 1030 and removing 1040 may be as described above for heating 720, maintaining 730 and removing 740 of FIG. 7. In one example, the heating 1020 may be performed above 200° C., and the maintaining 1030 and subsequent removing 1040 may provide empty channels and at least one 3D vascular network throughout the composite.

Optionally introducing 1050 a fluid into at least a portion of the microfluidic channels may include any of a variety of methods for introducing a fluid into a microfluidic channel, as described above for introducing 750 of FIG. 7. In one example, a microvascular composite is filled with at least one fluid having the desired physical properties to create a multifunctional material.

The presence of partially degradable polymeric fibers in a woven fiber preform can provide seamless fabrication of microvascular composites that are both strong and multifunctional. Preferably the hollow channels produced in the composites are high-fidelity inverse replicas of the original fibers' diameters and trajectories. Use of methods 700 and/or 1000 can provide microvascular fiber-reinforced composites with channels over one meter in length that then can be filled with a variety of fluids including aqueous solutions, organic solvents, and liquid metals.

Methods 700 and 1000 are examples of a method referred to as Vaporization of Sacrificial Components (VaSC). The VaSC methods can provide composite materials that include microfluidic channels having a range of channel curvatures and diameters, allowing the construction of a wide variety of network architectures. The methods also can provide composite materials that include microfluidic channels that are interconnected and/or branched.

When incorporated into a matrix of another material, a thermally degradable polymeric core containing a poly (hydroxyalkanoate) including an alkali earth metal or a transition metal, where the concentration of the metal in the fiber matrix is at least 0.1 wt %, preferably may be removed by heating at 200° C. The heating and removal may occur over the course of several minutes to several hours. Preferably the heating and removal are completed in at most 24 hours, at most 5 hours, at most 3 hours, or at most 2 hours. Details regarding the formation, degradation and removal of poly(hydroxyalkanoate) fibers is described, for example, in U.S. patent application Ser. No. 13/416,002, filed Mar. 9, 2012, with inventors Esser-Kahn et al., which is incorporated herein by reference.

The clearing of lactide from channels formed by degradation of PLA fibers including an alkali earth metal or a transition metal typically may result in a very low number of obstructions. Hidden defects in the channels may be present, and may be caused by complex channel geometries. Defects may be detected by calculating a theoretical value for pressure drop according to the Hagen-Pouiselle relation and comparing the prediction with a measured pressure head for the channels. A negligible difference from between these values indicates geometric uniformity and substantially complete channel clearing.

Partially degradable polymeric fibers having a thermally degradable polymeric core that includes a poly(hydroxyalkanoate) including an alkali earth metal or a transition metal, where the concentration of the metal in the fiber matrix is at least 0.1 wt %, preferably are compatible with fiber preform fabrication. Preferably the single fiber tension strength of a partially degradable polymeric fiber exceeds the threshold stress of 23 MPa applied during automated weaving. Preferably the single fiber tension strength of a partially degradable polymeric fiber is at least 30 MPa, at least 50 MPa, at least 75 MPa, or at least 100 MPa.

Uses of Microvascular Systems

Microvascular networks capable of independent fluid flow and/or controlled mixing between fluids are relevant for a range of applications in microfluidics and self-healing systems. A variety of properties may be obtained with a single microvascular system by selection of one or more fluids for introduction to the microchannels. The variation in properties can be obtained without varying the composite's form factor. Examples of materials properties that may be affected by the fluid in the microchannels of the composites include thermal management, electro-magnetic signature, electrical conductivity tuning, and chemical reactivity.

A microvascular system that includes independent microfluidic channels having independent fluid flow may include modified surfaces within some or all of the microfluidic channels. For example, one plurality of interconnected microfluidic channels in a system may have a hydrophilic surface at the interior of its channel walls, while another plurality of interconnected microfluidic channels in a system may have a hydrophobic surface at the interior of its channel walls. Hydrophilic and/or hydrophobic surfaces at the interior of microfluidic channel walls may be formed by any of a variety of known techniques, including those listed above with regard to applying a surface treatment to the solid polymeric coating as part of the depositing (240, 350). Hydrophilic and/or hydrophobic surfaces at the interior of microfluidic channel walls may be formed using photocleavable self-assembled monolayers (SAMs) as described in Zhao et al., *J. Am. Chem. Soc.* 124(19), 2002, 5284-85. It may also be desirable to modify the interior of microfluidic channels in microvascular systems that do not include independent channels.

Figure 11:
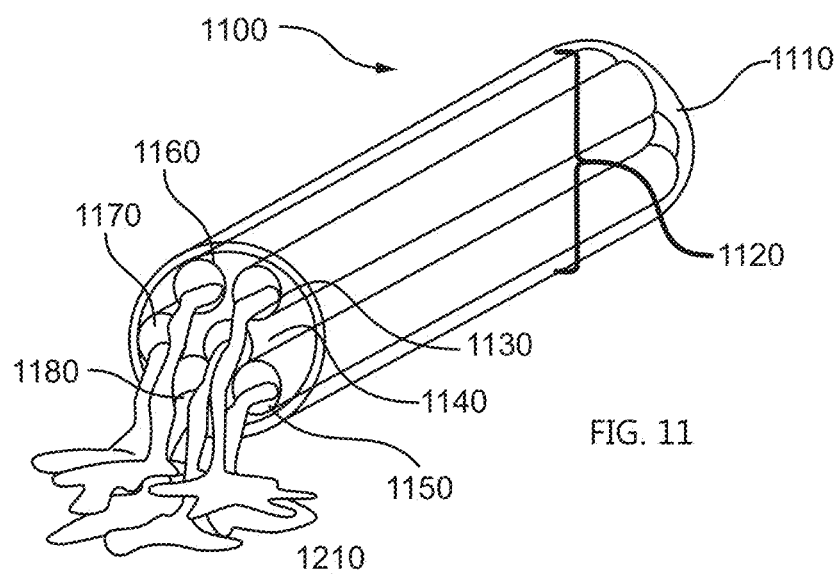
FIG. 11 depicts a microvascular system having independent microchannels.

FIG. 11 depicts a microvascular system 1100, which includes a solid polymeric matrix 1110 and a microchannel structure 1120 in the matrix. The microchannel structure 1120 includes independent microfluidic channels 1130, 1140, 1150, 1160, 1170 and 1180. As the channel walls of the independent microfluidic channels are impermeable, the fluids within the channels flow without mixing.

Figure 12:
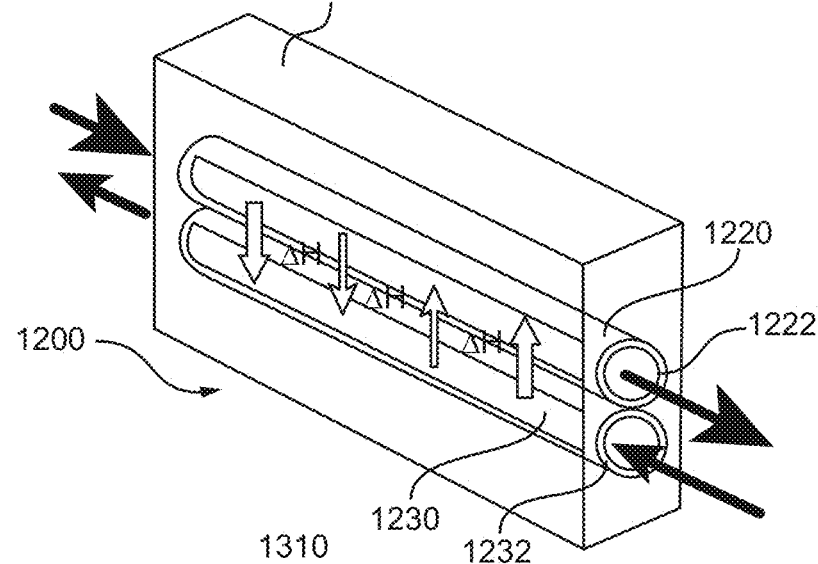
FIG. 12 depicts a microvascular system having microchannels in thermal communication.

FIG. 12 depicts a microvascular system 1200, which includes a solid polymeric matrix 1210, a first microfluidic channel 1220 in the matrix, and a second microfluidic channel 1230 in the matrix. The first microfluidic channel 1220 has a channel wall 1222, and the second microfluidic channel 1230 has a channel wall 1232. The microfluidic channel walls 1222 and 1232 are impermeable; however, the channel walls can conduct heat. Thus, the first and second microfluidic channels can transfer energy, in this instance in the form of heat, between the fluids in the channels.

Figure 13:
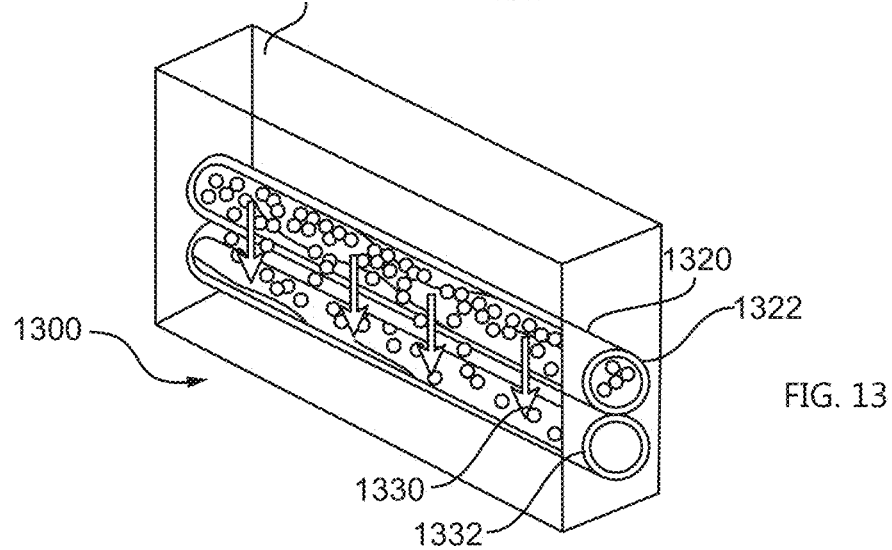
FIG. 13 depicts a microvascular system having microchannels in fluid communication.

FIG. 13 depicts a microvascular system 1300, which includes a solid polymeric matrix 1310, a first microfluidic channel 1320 in the matrix, and a second microfluidic channel 1330 in the matrix. The first microfluidic channel 1320 has a channel wall 1322, and the second microfluidic channel 1330 has a channel wall 1332. The microfluidic channel walls 1322 and 1332 are permeable, which allows for the transfer of mass, in this instance in the form of fluid, between the two microfluidic channels.

One example of a microvascular system having permeable channel walls is a water purification system. A microvascular water purification system includes a first plurality of microfluidic channels and a second plurality of microfluidic channels, where the first and second channels are separated by channel walls containing a nanoporous polymer. A first stream of water having a high concentration of dissolved salts is introduced into the first plurality of channels and flows through the first channels as a pressure is applied. A second stream of water having a low or negligible concentration of dissolved salts is introduced into the second plurality of channels. The osmotic pressure difference between the two liquids causes water to pass from the second stream into the first stream, diluting the first stream and reducing the concentration of dissolved salts in the first stream.

Another example of a microvascular system having permeable channel walls is an energy production system. An energy production system includes a first plurality of microfluidic channels and a second plurality of microfluidic channels, where the first and second channels are separated by channel walls containing an ionic separator. A cathode fluid is introduced into the first plurality of channels and flows through the first channels as a pressure is applied. An anode fluid is introduced into the second plurality of channels and flows through the second channels as a pressure is applied. Ions can pass between the fluids through the ionic separator, creating a flow of charge that can be collected on the opposite sides of the first and second pluralities of microfluidic channels. The collected charge flow can then be converted into a conventional electrical current.

Microporous Films

It has also been discovered that microporous films may be made from coating precursors that include a thermally degradable polymeric material and a thermally stable material having a degradation temperature higher than the degradation temperature of the thermally degradable polymeric material. A coating precursor is cast into a film that is subject to depolymerization of the thermally degradable polymeric material, to produce a microporous film. Preferably, the microporous film has a thickness of from 3 μm to 50 μm, and more preferably of from 5 μm to 30 μm. Preferred average pore sizes are between 50 nm to 10 μm, and more preferred average pore sizes range between 100 nm to 5 μm.

The thermally degradable polymeric material preferably has a degradation temperature below 280° C., and preferably has a degradation temperature of at most 250° C. Preferably the thermally degradable polymeric material has a degradation temperature between 100 and 250° C. Preferably the thermally degradable polymeric material has a degradation temperature of at most 220° C., of at most 180° C., of at most 150° C., or of at most 100° C. The thermally degradable polymeric material may include a poly(hydroxyalkanoate). Examples of poly(hydroxyalkanoate)s include poly(3-hydroxybutyrate) (P3HB), poly(4-hydroxybutyrate) (P4HB), poly(3-hydroxy-valerate) (PHV), polycaprolactone, poly(lactic acid) (PLA), poly(glycolic acid) (PGA), and copolymers of the monomeric units of these polymers.

Preferably the poly(hydroxyalkanoate) has a weight average molecular weight (Mw) of at least 2,000, and a degradation temperature below 280° C. More preferably, the poly(hydroxyalkanoate) has a degradation temperature of at most 250° C. Optionally, the depolymerization temperature of poly(hydroxyalkanoate)s such as PLA may be reduced by blending the poly(hydroxyalkanoate) with an alkaline earth metal and/or a transition metal. Preferably, the concentration of the metal in the film is at least 0.1 percent by weight (wt %). Preferably the concentration of the metal in the film is at least 0.2 wt %, at least 0.5 wt %, at least 1 wt %, at least 2 wt %, at least 2.5 wt %, at least 3 wt %, at least 5 wt %, at least 7 wt %, or at least 10 wt %. The concentration of the metal in the film may be from 0.1 to 10 wt %, from 0.2 to 7 wt %, from 0.5 to 5 wt %, or from 1 to 3 wt %. Preferably the metal is present in the film as MgO, CaO, BaO, SrO, tin(II) acetate, tin(II) oxalate, tin(II) octoate, or scandium triflate (Sc(OTf)$_3$). More preferably the metal is present in the film as strontium oxide, tin(II) oxalate or tin(II) octoate.

When the film is heated to the degradation temperature of the thermally degradable polymeric material, the thermally degradable polymeric material will degrade to form degradants that can be removed, providing a microporous film containing the thermally stable material. In instances where the thermally degradable polymeric material has a degradation temperature of at most 250° C., the thermally stable material does not thermally degrade at temperatures below 250° C. Preferably, the thermally stable material does not thermally degrade at temperatures below 275° C., at temperatures below 280° C., at temperatures below 300° C., at temperatures below 325° C., or at temperatures below 350° C.

The thermally stable material may include a thermally stable polymeric material having a degradation temperature higher than the degradation temperature of the poly(hydroxyalkanoate), for example a polyamide such as nylon; a polyester such as poly(ethylene terephthalate) and polycaprolactone; a polycarbonate; a polyether; an epoxy polymer; an epoxy vinyl ester polymer; a polyimide such as polypyromellitimide (for example KAPTON®); a phenolformaldehyde polymer such as bakelite; an amine-formaldehyde polymer such as a melamine polymer; a polysulfone; a poly(acrylonitrile-butadiene-styrene) (ABS); a polyurethane; a polyolefin such as polyethylene, polystyrene, polyacrylonitrile, a polyvinyl, polyvinyl chloride and poly(D-CPD); a polyacrylate such as poly(ethyl acrylate); a poly(alkylacrylate) such as poly(methyl methacrylate); a polysilane such as poly(carborane-silane); and/or a polyphosphazene.

The thermally stable polymeric material may include an elastomer, such as an elastomeric polymer, an elastomeric copolymer, an elastomeric block copolymer, and/or an elastomeric polymer blend. Examples of elastomer polymers include polyolefins, polysiloxanes such as poly(dimethylsiloxane) (PDMS), polychloroprene, and polysulfides; examples of copolymer elastomers may include polyolefin copolymers and fluorocarbon elastomers; examples of block copolymer elastomers may include acrylonitrile block copolymers, polystyrene block copolymers, polyolefin block copolymers, polyester block copolymers, polyamide block copolymers, and polyurethane block copolymers; and examples of polymer blend elastomers include mixtures of an elastomer with another polymer.

The thermally stable material may include other ingredients in addition to the thermally stable polymeric material. For example, the thermally stable material may contain one or more particulate fillers, stabilizers, antioxidants, flame retardants, plasticizers, colorants and dyes, fragrances, or adhesion promoters. One type of adhesion promoter that may be present includes substances that promote adhesion between the thermally stable material and the thermally degradable material, and substances that promote adhesion between the thermally stable material and a polymeric matrix in which the thermally degradable material is contained.

In instances where the thermally stable material includes a polyimide, the Mw of the polyimide is at least 2,000. Soluble polyimides are preferred, such as the commercially available MATRIMID® 5218 (Lindberg & Lund A S, Ski, Norway) P84® (Evonik Industries, Essen, Germany), and mixtures thereof. Microporous polyimide films, such as the PI films of FIG. 20, can be produced by heating the film and depolymerizing the thermally degradable polymeric material. The microporous films have been found to be thermally and electrochemically stable, and to also allow the passage of lithium ions, and may be used in a variety of applications, for example as separator in energy storage devices such as batteries and electrolytic capacitors. Their mechanical strength and low thermal shrinkage can improve the safety of lithium-ion batteries, where their ability to keep their shape at high temperatures may prevent direct contact between positive electrode materials and negative electrode materials.

Methods of Making Microporous Films

Figure 22:
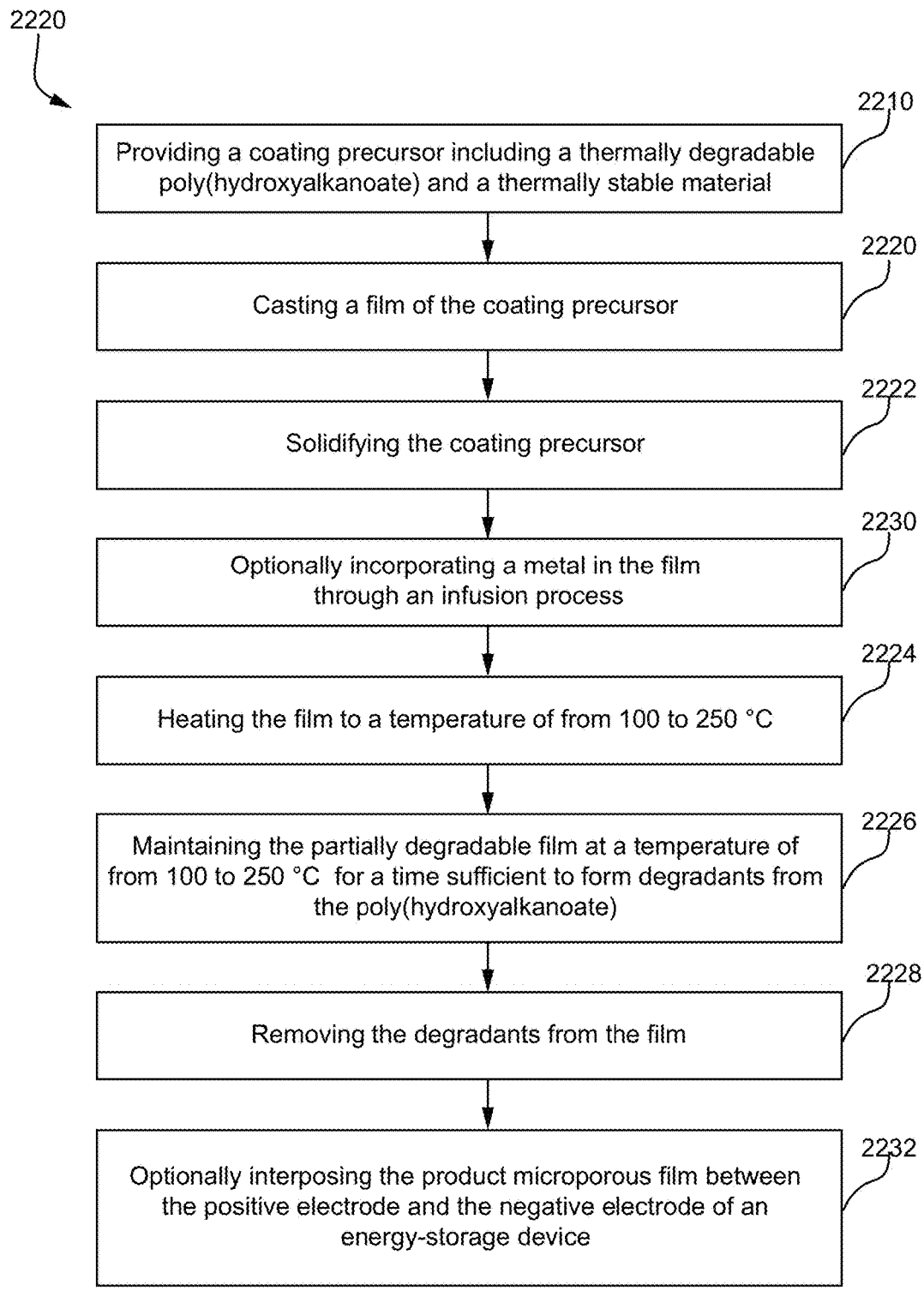
FIG. 22 is a schematic representation of a method of making a microporous film.

FIG. 22 illustrates a schematic representation of an exemplary VaSC method of making a microporous film. Method 2200 includes providing 2210 a coating precursor that includes a thermally degradable poly(hydroxyalkanoate) and a thermally stable material. Preferred thermally stable materials include thermally stable polymers, for instance polyimides because of their thermal stability at temperature typical of VaSC methods, their mechanical properties, and their solubility in solvents traditionally used for solubilizing polyhydroxyalkanoates. The coating precursor may be a solution formed by co-dissolving or co-dispersing the poly(hydroxyalkanoate) and the thermally stable material in a solvent. Method 2200 further includes casting 2220 a film of the coating precursor, for example by either a spin coating method or doctor blading method. Method 2200 also includes solidifying 2222 the coating precursor by removing at least a portion of the solvent from the coating precursor and/or chemical reaction (i.e. curing) of the coating precursor to form a solid film.

Preferably, the coating precursor is solidified at a temperature below the degradation temperature of the thermally degradable poly(hydroxyalkanoate). The solidification of the coating precursor to form a film may include removal of solvent from the precursor and/or chemical reaction (i.e. curing) of the precursor. Examples of solidification temperatures include 30° C., 50° C., 75° C., 100° C., 125° C., 150° C. and 180° C. Optionally, a surface treatment may be applied to the film. Examples of surface treatments include functionalization of the film by contacting the film with an oxidizing or reducing atmosphere or by contacting the film with a liquid containing a functionalizing reagent. Examples of surface treatments include applying an adhesion promoter to the film.

Method 2200 further includes heating 2224 the film to a temperature of from 100 to 250° C., maintaining 2226 the film at a temperature of from 100 to 250° C. for a time sufficient to form degradants from the poly(hydroxyalkanoate), and removing 2228 the degradants from the film to provide a microporous film. The degradants preferably have an average molecular weight less than 500 Daltons. Method 2220 may also include interposing 2232 the product microporous film between the positive electrode and the negative electrode of an energy-storage device, such as a lithium ion battery, to provide a separator between the positive electrode materials and the negative electrode materials.

The depolymerization temperature of poly(hydroxyalkanoate)s such as PLA may be reduced by the presence in the film of an alkaline earth metal and/or a transition metal. Preferably the concentration of the metal in the film is at least 0.2 wt %, at least 0.5 wt %, at least 1 wt %, at least 2 wt %, at least 2.5 wt %, at least 3 wt %, at least 5 wt %, at least 7 wt %, or at least 10 wt %. The concentration of the metal in the film may be from 0.1 to 10 wt %, from 0.2 to 7 wt %, from 0.5 to 5 wt %, or from 1 to 3 wt %. Preferably the metal is present in the film as MgO, CaO, BaO, SrO, tin(II) acetate, tin(II) oxalate, tin(II) octoate, or scandium triflate (Sc(OTf)$_3$). More preferably the metal is present in the film as strontium oxide, tin(II) oxalate or tin(II) octoate.

In one example, a metal selected from the group consisting of an alkali earth metal and a transition metal may be included in the coating precursor. In another example, method 2220 may include incorporating 2230 the metal in the film through an infusion process. A representative infusion process includes contacting the film with a composition including a fluorinated fluid, and a metal selected from the group consisting of an alkali earth metal and a transition metal, maintaining the film and the composition together at a temperature and for a time sufficient to provide a concentration of the metal in the film of at least 0.1 wt %, and separating the film and the fluorinated fluid. In one example, films may be infused with a tin(II) oxalate (SnOx) catalyst present in an aqueous trifluoroethanol (TEE) mixture.

In a set of representative examples, a coating precursor includes a monomer and/or prepolymer that can polymerize to form a polymer, such as a thermally stable polymer as described above with regard to the thermally stable polymeric material. The coating precursor may then be solidified by polymerizing the monomer and/or prepolymer of the precursor to form the film. Examples of monomers and/or prepolymers that can polymerize to form a polymer include cyclic olefins; unsaturated monomers such as acrylates, alkylacrylates (including methacrylates and ethacrylates), styrenes, isoprene and butadiene; lactones (such as caprolactone); lactams; epoxy-functionalized monomers, prepolymers or polymers; functionalized siloxanes; and two-part precursors for polymers such as polyethers, polyesters, polycarbonates, polyanhydrides, polyamides, formaldehyde polymers (including phenol-formaldehyde, urea-formaldehyde and melamine-formaldehyde), and polyurethanes. Polymerization of a coating precursor may include cross-linking of monomers and/or prepolymers to form an insoluble polymer network. Crosslinking may be performed by a variety of methods, including the addition of chemical curing agents and/or exposure to radiation such as infrared radiation (IR; i.e. heat), visible light, or ultraviolet radiation (UV).

The following examples are provided to illustrate one or more preferred embodiments of aspects of the present application. Numerous variations can be made to the following examples that lie within the scope of the present application.

EXAMPLES

Materials & Procedures

PLA pellets (Mw=339,000) for forming fibers by solution spinning were used as received from Purac Biomaterials. Catalyst tin(II) octoate was obtained from Sigma-Aldrich. Trifluoroethanol (TEE) was obtained from Halogen Inc. Polyimide resin was obtained from Alfa Aesar. Other chemicals were all obtained from Sigma-Aldrich unless otherwise noted.

Diglycidyl ether of bisphenol A resin (DGEBA or EPON® 828 was used as received from Miller-Stephenson (Danbury, Conn.), and the curing agent EPIKURE® 3300 was used as received from Hexion (Columbus, Ohio). Epoxy samples were prepared using a mass ratio of 22.7 parts per hundred (pph) EPIKURE® 3300 to EPON® 828.

Fiber surface morphology and fiber removal in epoxy matrices were imaged using a Leica DMR Optical Microscope at various magnifications. Image) software was used to measure fiber diameters from acquired images for each batch of fibers produced and to measure the fraction of PLA fiber removed.

Environmental Scanning Electron Microscopy (ESEM, Philips XL30ESEM-FEG) was used to image cross-sections of the holomatrix and to image empty channels. SEM images were acquired after sputter-coating the sample surface with carbon or gold-palladium, and were collected using backscattered electrons. Selected area elemental analysis was performed by EDS (Energy Dispersive X-ray Spectroscopy, attached to the SEM) with a 20 kV electron source and spot size of 3.0 nm.

An Xradia BioCT (MicroXCT-400) was used to image the apomatrix at 40 keV (8 W power and 200 µA current) at a 4× objective for 5 s exposure times. Rotation intervals were 0.25° for a complete 360° scan. Images were visualized in 3D with XM3Dviewer and reconstructed in 3D using XMReconstructor. Reconstructed images were reproduced in Amira to enhance the color and contrast.

Example 1: Formation of Thermally Degradable PLA Fibers

A PLA solution was prepared by dissolving 6 g of PLA pellets in dichloromethane at room temperature, and then removing solvent to provide a solution volume of 35 mL. Catalysts (tin(II) oxalate particles or tin(II) octoate liquid) were blended into the viscous PLA solution to provide a 10 wt % tin equivalence to PLA. The mixture was stirred for half an hour to disperse the catalyst, resulting in a spinning solution.

A spin chamber was pre-heated to 55° C., and 10 mL of the spinning solution was transferred to the chamber. The solution was conditioned in the spin chamber for 5 minutes, and then conditioned outside the chamber for additional 5 minutes before extrusion, allowing the solution to become more concentrated. The spinning solution was then extruded at 55° C. through the chamber at an extrusion speed of 8 cm/hr. The solution passed through a spinneret having a diameter from 0.2 mm to 1 mm, forming a single fiber. Two heating chambers below the spinneret provided additional heat to further evaporate the solvent. The extruded fiber filament was collected on a Teflon bobbin without applying additional stress, and was then air-dried at 50° C. The diameter of the fibers after drying was dependent on the diameter of the spinneret used in the spinning process. A spinneret diameter of 0.25 mm provided a final fiber diameter of 0.14±0.02 mm, a spinneret diameter of 0.50 mm provided a final fiber diameter of 0.42±0.03 mm, and a spinneret diameter of 1.00 mm provided a final fiber diameter of 0.75±0.05 mm.

SEM analysis of the fibers confirmed a uniform distribution of the SnOc in the spun PLA fiber, which is believed to provide a uniform catalyzed depolymerization reaction upon heating, resulting in rapid clearing of the channel formed from degradation and removal of the fiber core.

The mechanical properties of the spun PLA fibers could be changed by cold-drawing the spun fibers. Cold-drawing fibers may provide an increase in tensile strength, which is theorized to be due to alignment of the individual polymer chains within the fiber during the drawing process. WAXS analysis of PLA fibers that were cold-drawn after being spun was consistent with an increase in polymer chain alignment within these fibers, as the degree of orientation of pure spun PLA fiber (no catalyst) increased from 0% when no drawing was performed to 23% when cold-drawing was performed. Spun PLA fibers were drawn to different draw ratios, and their failure strengths were studied by a single fiber tension test. Cold-drawing appeared to significantly increase the fiber strength, whereas the presence of SnOc catalyst did not appear to affect fiber failure strength significantly. As the measured fiber failure strengths were greater than 23 MPa, the fibers were expected to survive the weaving process without significant failure.

Example 2: Formation of Partially Degradable Fibers

Thermally degradable PLA fibers according to Example 1 were coated with a polysiloxane. A thermally degradable PLA fiber was unwound using a tensioner, and then passed through a bath containing a coating precursor containing a liquid copolymer of dimethylsiloxane (DMS) and (epoxy-cyclohexyl)ethylmethylsiloxane (ECMS), and containing the cationic polymerization initiator (p-isopropylphenyl)(p-methlyphenyl) iodonium tetrakis(pentafluorophenyl)borate. The cationic initiator can initiate the reaction of the epoxy groups in the poly(ECMS-co-DMS) when subjected to UV irradiation.

The fiber was then pulled through a syringe needle tip that had an inner diameter greater than the diameter of the fiber, providing a uniform layer of the coating precursor on the exterior surface of the fiber. UV radiation was then applied to the coating precursor on the fiber, curing the poly(ECMS-co-DMS) into a crosslinked polysiloxane. The resulting coated fiber was collected on a take-up drum.

The thickness of the coating correlated with the difference between the fiber diameter and the inner diameter of the syringe needle tip through which the fiber was pulled after passing through the bath. Table 1 lists a variety of fiber diameters, syringe needle tip inner diameters, and resulting coated fiber diameters.

TABLE 1

Radial dimensions of PLA fibers, syringe needle tips, and PLA fibers coated with polysiloxane.

| Diameter of PLA fiber (µm) | Inner diameter of syringe needle tip (µm) | Diameter of coated PLA fiber (µm) |
| --- | --- | --- |
| 200 | 250 | 230 |
|  | 330 | 270 |
| 300 | 410 | 350 |
|  | 510 | 400 |
| 500 | 610 | 700 |

Figure 14:
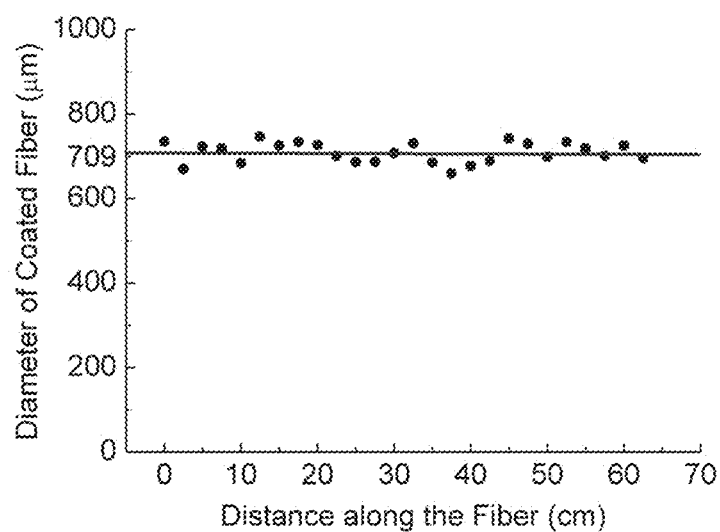
FIG. 14 represents a graph of the diameter of a coated fiber as a function of the distance along the fiber.

The thickness of the coating was relatively uniform along the length of the coated fiber. FIG. 14 is a graph of the diameter of a coated fiber as a function of length along the fiber. For a length of 65 centimeters, the diameter of the coated fiber varied from 650 to 750 µm, a variation of 7% from the mean diameter of 709 µm (7.05%=(50 µm/709 µm)×100%).

Example 3: Formation of Composite Containing Partially Degradable Fibers

Coated fibers according to Example 2 were embedded in an EPON® 828: EPIKURE® 3300 epoxy thermoset matrix. The coated fibers were held straight in RTV Silicone molds before filling the mold with epoxy. EPON® 828 epoxy resin and a cycloaliphatic amine curing agent EPIKURE® 3300 were mixed at a ratio of 100:22.7 parts by weight and degassed until air bubbles ceased to form. The post-curing cycle involved heating the specimens at 82° C. for 90 minutes followed by 150° C. for an additional 90 minutes. The cured epoxy thermoset composites were carefully trimmed before thermal treatment to expose fiber ends.

Figure 15:
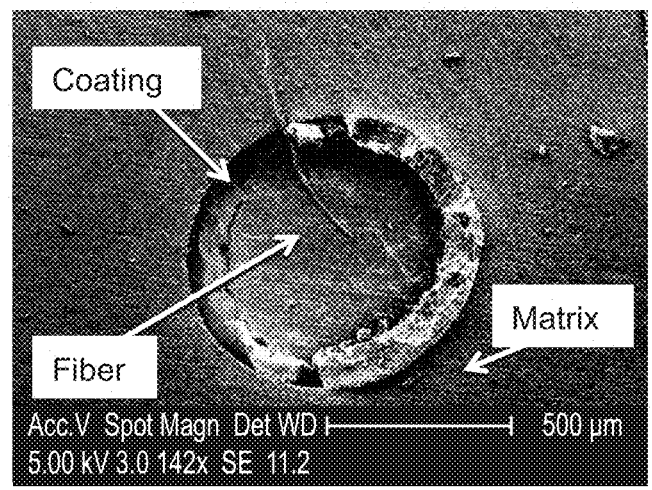
FIG. 15 depicts a scanning electron microscopy (SEM) image of a composite material containing a partially degradable polymeric fiber.

FIG. 15 depicts a scanning electron microscopy (SEM) image of the composite. The PLA fiber, having a diameter of 500 µm, is in the center, surrounded by the poly(dimethylsiloxane) coating, which in turn is surrounded by the epoxy thermoset matrix.

Example 4: Formation of Microvascular System Containing Independent Microfluidic Channels A composite was formed according to Example 3, where the composite included the epoxy thermoset matrix, and two coated PLA fibers in the matrix. The two coated fibers each included a thermally degradable PLA core and a polysiloxane coating. The two coated fibers were arranged perpendicularly and in physical contact at their intersection. After the epoxy was cured, the composite was heated in a sealed vacuum oven (Fisher Isotemp 283) at 200° C. under vacuum (1 torr) for 2 hours, resulting in degradation and removal of the PLA fiber cores.

Figure 16:
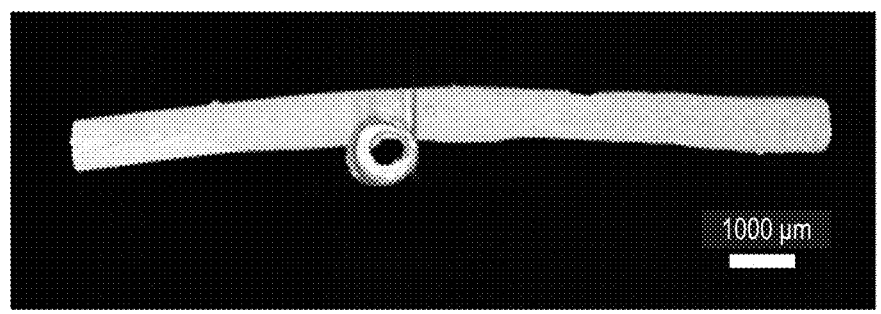
FIG. 16 depicts a micro-CT image of two independent channels formed from two partially degradable polymeric fibers.

FIG. 16 depicts a MicroCT image of the microvascular system formed from the composite. The system included two microfluidic channels arranged perpendicularly, and the empty channel within the polysiloxane channel wall was observed in the orthogonal channel.

Example 5: Demonstration of Fluid Non-Communication Between Independent Microfluidic Channels in a Microvascular System A composite was formed according to Example 3, except that the solid polymer matrix was poly(dimethylsiloxane) (PDMS) formed using the two-component siloxane kit Sylgard® 184 (DOW CORNING), which contained a mixture of hydroxyl terminated polydimethylsiloxane (HOPDMS) with polydiethylsiloxane (PDES). The composite included the PDMS matrix and two coated PLA fibers in the matrix. The two coated fibers each included a thermally degradable PLA core and a polysiloxane coating. The two coated fibers were in physical contact along the length at which the fibers were interwoven. After the PDMS was cured, the composite was heated in a sealed vacuum oven (Fisher Isotemp 283) at 200° C. under vacuum (1 torr) for 2 hours, resulting in degradation and removal of the PLA fiber cores.

Figure 17:
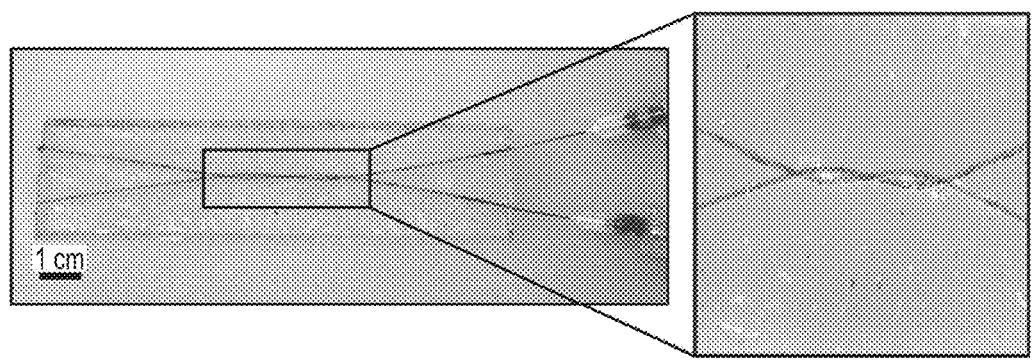
FIG. 17 depicts images of a composite material containing two independent channels formed from two partially degradable polymeric fibers.

FIG. 17 depicts an optical microscopy image of the microvascular system formed from the composite. The system included two independent microfluidic channels having impermeable channel walls. The lack of fluid communication between the two microfluidic channels was demonstrated by introducing an orange liquid into one channel and introducing a blue liquid into the other channel. No mixing of the colors was observed, which indicated that the liquids were not in fluid communication despite the physical contact between the microfluidic channels.

Example 5: Formation of Porous Polyester for Use as a Permeable Coating

Figure 18:
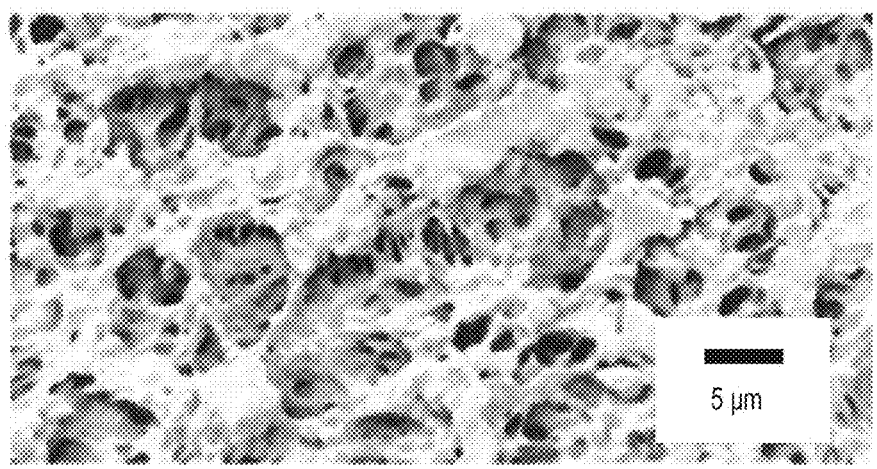
FIG. 18 depicts a SEM image of a porous polyester material.

A coating precursor was formed from a mixture of PLA and the polyester poly(ethylene terephthalate) (PET). A liquid mixture was prepared containing 6 weight percent (wt %) PET and 4 wt % PLA in a solvent that was a 70:30 mixture of dichloromethane and trifluoroacetic acid. The liquid mixture was cast into a film by spin-coating at 500 rpm. The film was then soaked in dichloromethane to remove the PLA. FIG. 18 depicts an SEM image of the resulting porous film.

Example 6: Formation of Porous Polyimide for Use as a Permeable Coating

Figure 19:
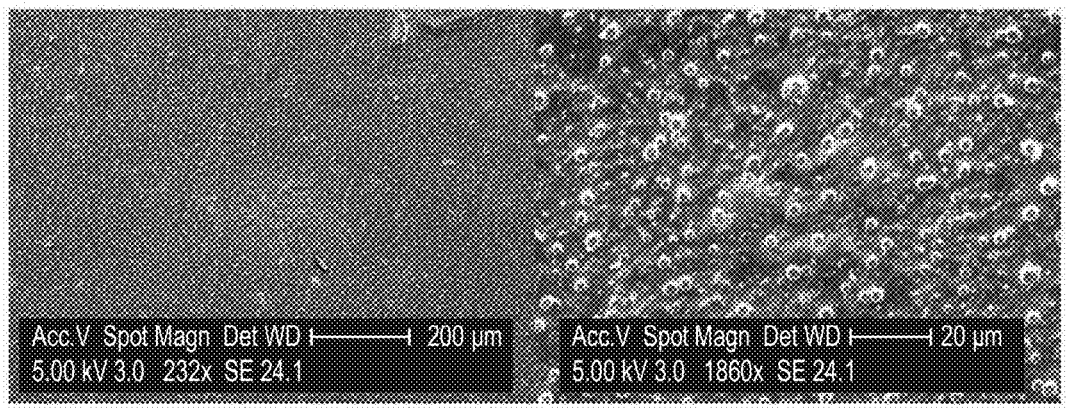
FIG. 19 depicts SEM images of a film containing a blend of polyimide and poly(lactic acid) (PLA).
Figure 20:
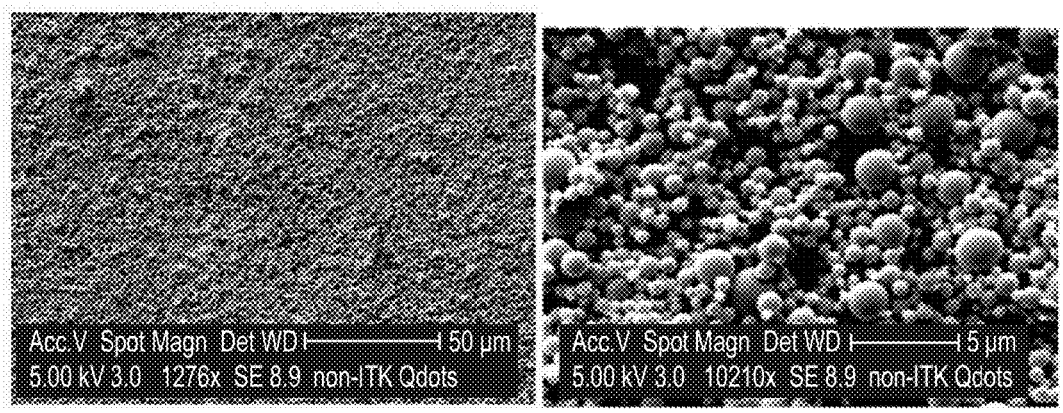
FIG. 20 depicts SEM images of the film according to FIG. 19 after thermal degradation and removal of the PLA.

A coating precursor was formed from a mixture of PLA and a polyimide. The polyimide was a soluble thermoplastic polyimide having a chemical name of 1,3-isobenzofurandione, 5,5'-carbonylbis-, polymer with 1- (or 3-) (4-aminophenyl)-2,3-dihydro-1,3,3 (or 1,1,3)-trimethyl-1H-inden-5-amine (CAS#62929-02-6). A solution was prepared containing from 1-2 wt % polyimide and from 1-1.5 wt % PLA in chloroform. The solution was cast into a film either by spin-coating or by contacting a layer of the solution with a doctor blade. The resulting polymer blend film had a thickness of from 5 to 30 μm. FIG. 19 depicts SEM images of the polymer blend film formed using a doctor blade. The microspheres are believed to be particles containing the polyimide. The polymer blend films were heated in a sealed vacuum oven (Fisher Isotemp 283) at 200° C. under vacuum (1 torr) for 2 hours, resulting in degradation and removal of the PLA phase. FIG. 20 depicts SEM images of the resulting porous film. The microspheres are believed to be particles containing the polyimide that have sintered together to form a cohesive film. The pores left by the removal of the PLA phase had widths of approximately 1 μm.

Figure 21:
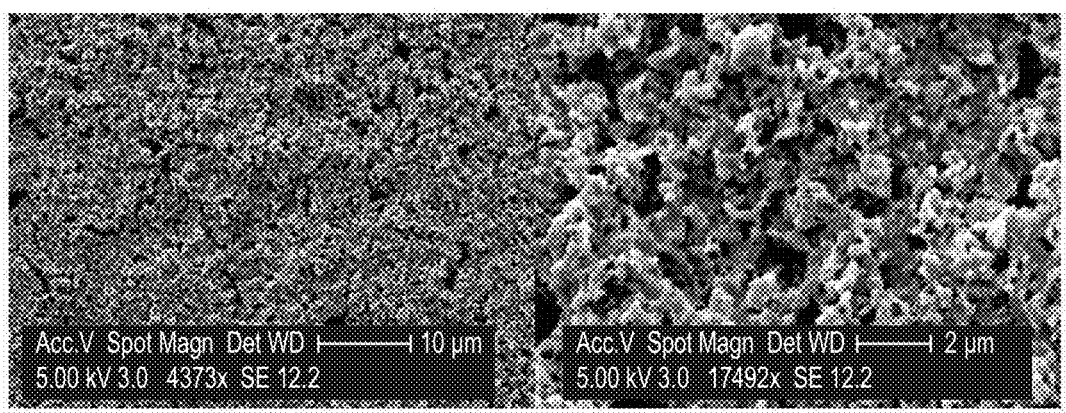
FIG. 21 depicts SEM images of a film formed from a bicontinuous film containing polyimide and PLA, after thermal degradation and removal of the PLA.

In another example, a coating precursor was formed from a mixture of PLA and a polyimide in a binary solvent. A solution was prepared containing from 1-2 wt % polyimide and from 1-1.5 wt % PLA in a solvent that was a 10:1 mixture of chloroform and dioxane. As described above, the solution was cast into a film and heated in a sealed vacuum oven (Fisher Isotemp 283) at 200° C. under vacuum (1 torr) for 2 hours, resulting in degradation and removal of the PLA phase. FIG. 21 depicts SEM images of the resulting porous film. As the PLA and polyimide formed a bicontinuous film when cast from the binary solvent, the resulting porous film had a continuous polyimide phase.

Example 7: Microporous Polyimide Battery Separators

The coating precursor of Example 6 was formed as solution having a PI:PLA ratio 40:60 (wt/wt) in chloroform. The PI was a 1,3-isobenzofurandione having a molecular weight of about 38 kDa, and the PLA of about 55 KDa. The solution was cast into a film either by spin coating or by contacting a film of the solution with a doctor blade, and the film was left to dry for 10 minutes. The resulting polymer blend film was heated in a sealed vacuum oven to a temperature of 280° C., removing the PLA and resulting in microporous polyimide films having a thickness of 5 to 30 μm.

Figure 23:
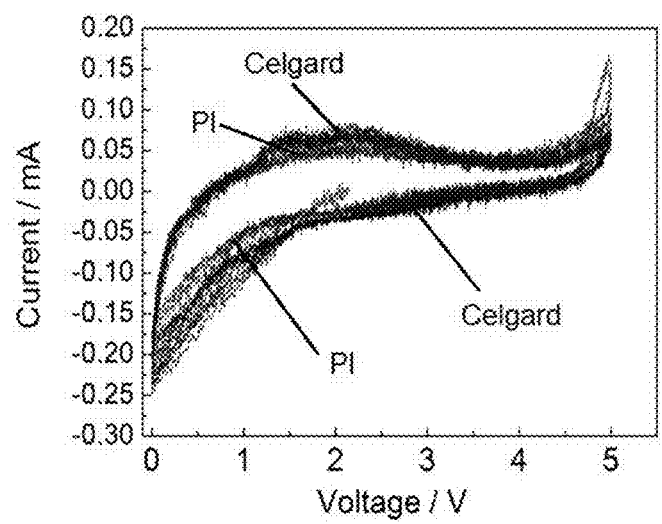
FIG. 23 depicts linear sweep voltammograms (LSV) of lithium-ion coin cells assembled with a microporous polyimide separator or a CELGARD® 2325 separator.

Button lithium-ion cells were prepared with a mesocarbon microbeads (MCMB) graphite powder (Enerland, Korea) as anode material, $Li(Ni_{1/3}Co_{1/3}Mn_{1/3})O_2$ (NMC) as cathode material, and $LiPF_6$ in ethylene carbonate (EC) as solvent. Cathodes and anodes were cut to the appropriate size using a 1.59 punch. A first set of batteries featured microporous polyimide separators having a thickness of 20 μm, and a second set of control batteries were fitted with CELGARD® 2325 (Celgard, Charlotte, N.C.), a type of traditional, commercially available trilayer (PP/PE/PP) separator membranes. The cells with the microporous polyimide separator exhibited impedance and discharge capacity values very close to those of coin cells featuring the Celgard® 2325. This is illustrated in the linear sweep voltammograms (LSV) of FIG. 23, which were taken on both types of cells (scan rate: 1.0 mV/s).

Figure 24A:
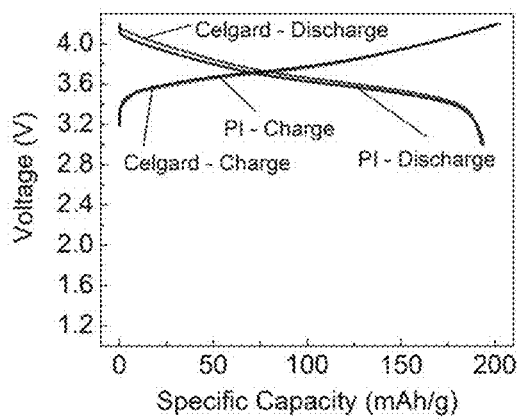
FIG. 24A represents galvanostatic plots for coin cells assembled with a microporous polyimide separator (40: 60=PI:PLA, 10 mins annealing) or with a CELGARD® 2325 separator as control. Only one cycle is shown.
Figure 24B:
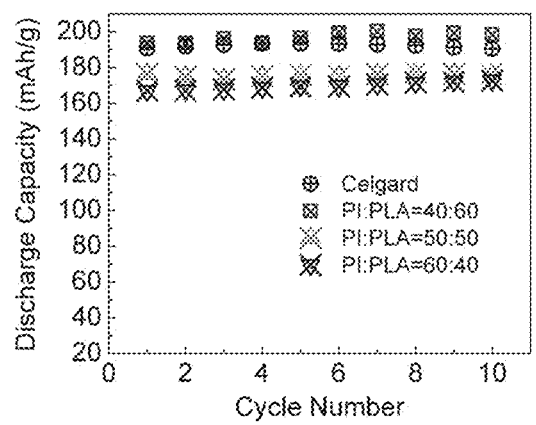
FIG. 24B represents a graph of the discharge capacities of coin cells assembled with microporous polyimide separators with different PI:PLA ratios (10 mins annealing time) or a CELGARD® 2325 separator as control. Data is shown for 10 cycles.
Figure 24C:
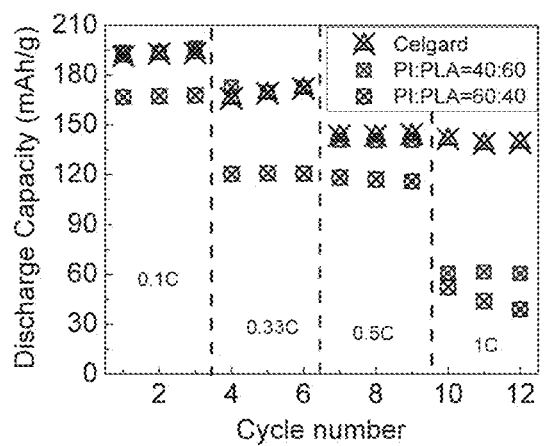
FIG. 24C represents a graph of discharge capacities for coin cells assembled with microporous polyimide separators (40:60=PI:PLA, 10 mins annealing) or with a CELGARD® 2325 separator as control. The discharge capacities were measured at C/10, C/5, C/2, and C/1 rates, respectively.

FIG. 24A illustrates the charge and discharge curves of a coin cell featuring the microporous polyimide separator, exhibiting a specific capacity of about 193.91 mAh/g with a capacity retention ratio of 96.3%, nearly the same as that of a coin cell assembled with a commercial CELGARD® 2325 separator (192.76 mAh/g, 95.1%). FIG. 24B illustrates the cycling behavior of coin cells featuring the microporous polyimide separator, as measured at a 0.1 C rate at room temperature; a stable cycling behavior was observed and no abnormal or unstable charge-discharge profiles were observed. Coin cells featuring microporous polyimide separators prepared from coating precursors having PI:PLA ratios of 50:50 and 60:40, respectively, exhibited a similar behavior. FIG. 24C illustrates the charge and discharge capacities of batteries featuring the polyimide separators as a function of the discharge current density (i.e., discharge C-rate). Noticeably, the discharge capacities dropped at higher discharge current densities, where the influence of ionic transport on the ohmic polarization (IR drop) is more significant. FIG. 24C shows that the polyimide separators allowed for successful battery cycling at different charge densities.

Figures 25A, 25B:
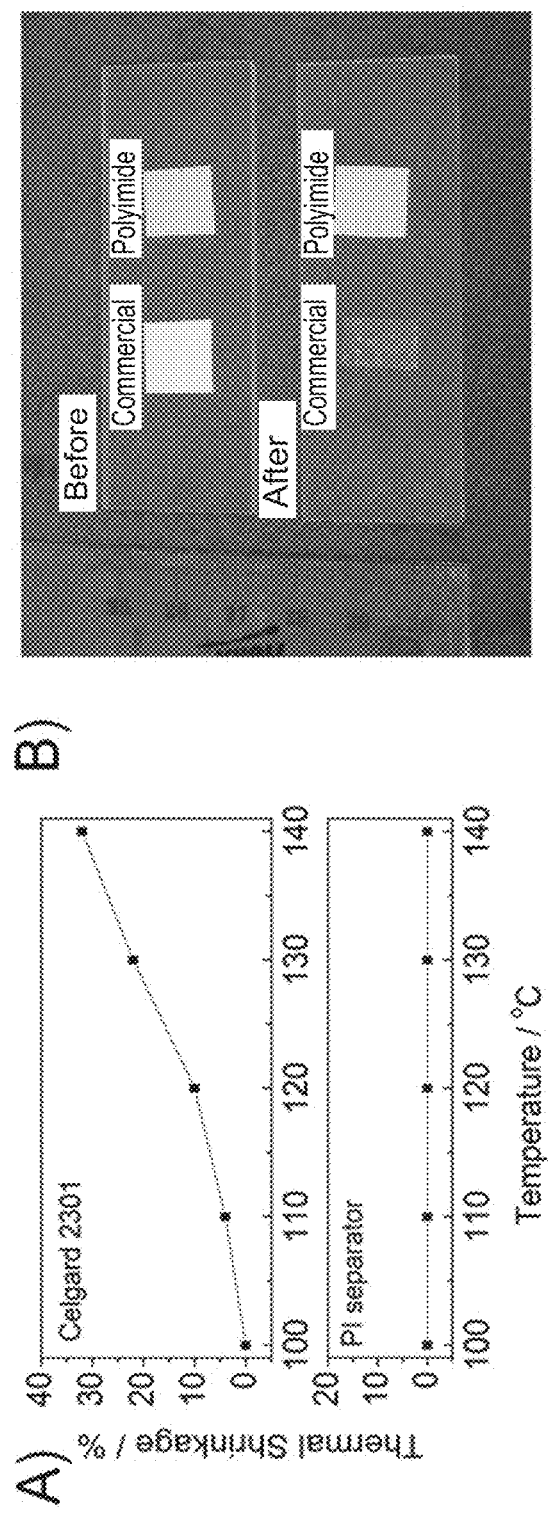
FIG. 25A represents a graph of thermal shrinkage measured at increasing temperatures for a microporous polyimide separator and a CELGARD® 2325 separator.
FIG. 25B depicts a photograph of a microporous polyimide separator and a CELGARD® 2325 separator before and after heat treatment at 140° C. for 30 minutes.

The thermal shrinkage of the microporous polyimide separators was assessed by changes in size (as measured by length and width) following heat treatment at various temperatures for 30 minutes. FIG. 25A illustrates how the polyimide separator hardly changed over a wide temperature range, whereas conventional, commercially available CELGARD® 2325 separators exhibited amounts of shrinkage that were directly proportional to the heat treatment temperature. This difference in thermal shrinkage between the two types of separators increased as the temperature of the heat treatment approached 140° C. FIG. 25B is a photograph of the microporous polyimide separator and of the CELGARD® 2325 separator prior to and following heat treatment at a temperature of 140° C. for 30 minutes. The CELGARD® 2325 separator underwent a thermal shrinkage of 32%. In contrast, the microporous polyimide separator showed little change due to thermal shrinkage. The microporous polyimide separator was thermally stable. Without wishing to be bound to any particular theory, this stability is believed to be a result of its melting temperature of more than 480° C. Therefore, it appears that the superior thermal stability of the polyimide prevents thermal shrinkage, thereby providing a safe, thermally stable battery separator.

Example 8: Formation of Sacrificial Fibers Coated with a PI/PLA Blend

Figure 26:
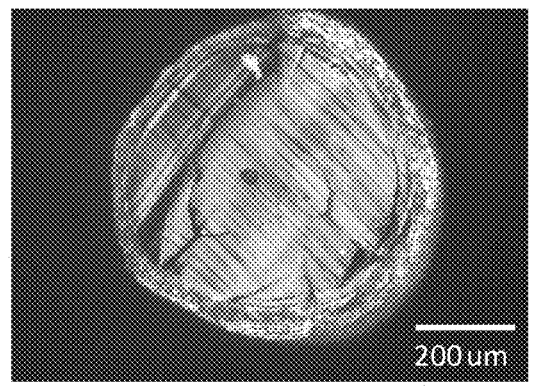
FIG. 26 depicts an optical micrograph of the cross-section of a PLA fiber with a PI/PLA coating.

A coating precursor was formed from a mixture of a soluble polyimide (Matrimid® 5218, number average molecular weight (Mn) 38,000; Mw 73,000) and PLA having a Mn of 55,400 (Natureworks, Minnetonka, Minn.). A solution was prepared containing 2-2.5 wt % polyimide, 1-1.5 wt % PLA, and 0.2-0.4 wt % tin(II) octoate in chloroform. Sacrificial fibers were dip-coated with the solution, leaving a coating containing a mixture of phase-separated polyimide and PLA. FIG. 26 shows an optical micrograph of the cross-section of a coated fiber.

Figure 27:
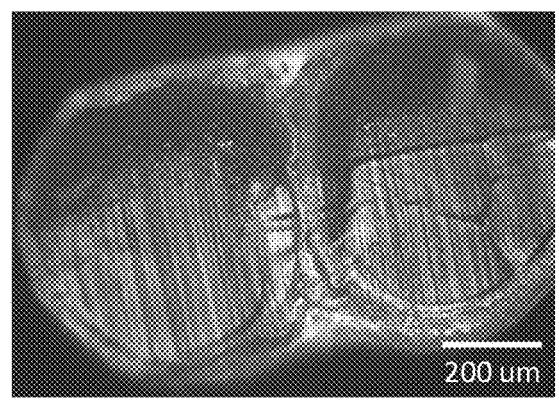
FIG. 27 depicts an optical micrograph of the cross-section of a set of PLA fibers held together with a PI/PLA coating.

In another example, sets of two PLA fibers held at a fixed proximity were dip-coated into a solution containing 2-2.5 wt % PI, 1-1.5 wt % PLA, and 0.2-0.4 wt % tin(II) octoate in chloroform. FIG. 27 shows an optical micrograph of the cross-section of the collectively coated fibers.

Definitions

To provide a clear and more consistent understanding of the specification and claims of this application, the following definitions are provided.

The term "polymeric" means a substance that includes a polymer.

The term "polymer" means a substance containing more than 100 repeat units. The term "polymer" includes soluble and/or fusible molecules having long chains of repeat units, and also includes insoluble and infusible networks. The term "prepolymer" means a substance containing less than 100 repeat units and that can undergo further reaction to form a polymer. Unless otherwise specified, polymer molecular weights are given in Daltons.

The term "matrix" means a continuous phase in a material.

The term "matrix precursor" means a composition that will form a polymer matrix when it is solidified. A matrix precursor may include a monomer and/or prepolymer that can polymerize to form a solid polymer matrix. A matrix precursor may include a polymer that is dissolved or dispersed in a solvent, and that can form a solid polymer matrix when the solvent is removed. A matrix precursor may include a polymer at a temperature above its melt temperature, and that can form a solid polymer matrix when cooled to a temperature below its melt temperature.

The term "woven structure" means a single ply of an assembly of threads, where the threads are oriented in at least 2 directions within the ply.

The term "microfluidic channel" means a substantially tubular structure having a diameter less than 1,000 micrometers.

The term "microfluidic network" means a plurality of channels having a plurality of interconnects, where at least a portion the channels have a dimension less than 1,000 micrometers.

The term "fluid communication" means that two objects are in an orientation, and within a sufficient proximity to each other, such that fluid can flow from one object to the other. The term "fluid" means a substance in the liquid or gaseous state. In one example, if a microfluidic channel embedded in a matrix is in fluid communication with a surface of the matrix, then fluid can flow from the channel onto the surface.

While various embodiments of the present application have been described, it will be apparent to those of ordinary skill in the art that other embodiments and implementations are possible within the scope of the present application. Accordingly, the present application is not to be restricted except in light of the attached claims and their equivalents.

What is claimed is:

1. A microvascular system, comprising:
    a solid polymeric matrix comprising a first material, and
    a woven structure in the matrix, the woven structure comprising microfluidic hollow channels having a channel wall comprising a second material,
    where the second material is different from the first material,
    where the microfluidic channels are formed from a plurality of partially degradable polymeric fibers comprising a thermally degradable polymeric core and a coating surrounding at least a portion of the thermally degradable polymeric core,
    where the coating comprises a thermally stable polymeric material having a degradation temperature higher than the degradation temperature of the thermally degradable polymeric core,
    where the thermally degradable polymeric core has been substantially thermally degraded and removed to form the hollow channels, and
    where the second material of the channel wall comprises the thermally stable polymeric material of the coating.

2. The microvascular system of claim 1, where the microfluidic channels have an average diameter of from 20 to 500 micrometers.

3. The microvascular system of claim 1, the woven structure further comprises a second plurality of microfluidic channels.

4. The microvascular system of claim 3, where the first and second plurality of microfluidic channels are in fluid communication.

5. The microvascular system of claim 4, where the channel wall is liquid permeable.

6. The microvascular system of claim 4, where the channel wall is impermeable.

7. The microvascular system of claim 3, where the first and second plurality of microfluidic channels are not in fluid communication.

8. The microvascular system of claim 1, where the woven structure comprises warp threads and weft threads in a 2D woven structure, and at least a portion of the microfluidic channels are present as warp threads.

9. The microvascular system of claim 1, where the woven structure comprises warp threads and weft threads in a 2D woven structure, and at least a portion of the microfluidic channels are present as weft threads.

10. The microvascular system of claim 1, where the woven structure comprises warp threads, weft threads and Z-threads in a 3D woven structure, and at least a portion of the microfluidic channels are present as weft threads or as Z-threads.

11. The microvascular system of claim 1, where the woven structure further comprises a plurality of reinforcing fibers.

12. The microvascular system of claim 11, where the reinforcing fibers are selected from the group consisting of carbon fibers and glass fibers.

13. The microvascular system of claim 1, where the solid polymer matrix comprises a polymer selected from the group consisting of a polyamide, a polyester, a polycarbonate, a polyether, an epoxy polymer, an epoxy vinyl ester polymer, a polyimide, an amine-formaldehyde polymer, a polysulfone, a poly(acrylonitrile-butadiene-styrene), a polyurethane, a polyolefin, a polyacrylate, a poly(alkylacrylate), a polysilane, a polyphosphazene.

14. The microvascular system of claim 1, where the thermally degradable polymeric core comprises a poly(hydroxyalkanoate) and a metal selected from the group consisting of an alkaline earth metal and a transition metal, where the concentration of the metal is at least 0.1 wt %.

15. The microvascular system of claim 1, where the thermally degradable polymeric core has a degradation temperature of at most 250° C., and the thermally stable polymeric material of the coating does not thermally degrade at temperatures below 275° C.

16. The microvascular system of claim 1, where the coating surrounds substantially the entire thermally degradable polymeric core.

17. The microvascular system of claim 1, where the thermally stable polymeric material of the coating comprises a polyimide, polyester, polycarbonate, polyether, epoxy polymer, epoxy vinyl ester polymer, polyamide, phenol-formaldehyde polymer, amine-formaldehyde polymer, polysulfone, polyacrylonitrile-butadiene-styrene, polyurethane, polyolefin, polystyrene, polyacrylonitrile, polyvinyl chloride, poly(DCPD), polyacrylate, poly(alkylacrylate), polysilane, polyphosphazene, or a combination thereof.

18. The microvascular system of claim 14, where the poly(hydroxyalkanoate) comprises poly(lactic acid), poly(3-hydroxybutyrate), poly(4-hydroxybutyrate), poly(3-hydroxy-valerate), polycaprolactone, poly(glycolic acid) and/or copolymers of monomeric units of the preceding polymers.

19. The microvascular system of claim 14, where the metal is selected from the group consisting of MgO, CaO, BaO, SrO, tin(II) acetate, tin(II) oxalate, tin(II) octoate, and scandium triflate (Sc(OTf)$_3$).

20. A microvascular system, comprising:
a solid polymeric matrix comprising a first material, and
a woven structure in the matrix, the woven structure comprising microfluidic hollow channels having a channel wall comprising a second material,
where the second material is different from the first material,
where the microfluidic channels are formed from a plurality of partially degradable polymeric fibers comprising a thermally degradable polymeric core and a coating surrounding at least a portion of the thermally degradable polymeric core,
where the coating comprises a thermally stable polymeric material having a degradation temperature higher than the degradation temperature of the thermally degradable polymeric core,
where the thermally degradable polymeric core comprises a poly(hydroxyalkanoate) and a metal selected from the group consisting of an alkaline earth metal and a transition metal, where the concentration of the metal is at least 0.1 wt %,
where the thermally degradable polymeric core has been substantially thermally degraded and removed to form the hollow channels, and
where the second material of the channel wall comprises the thermally stable polymeric material of the coating.

* * * * *